(12) United States Patent
Blake

(10) Patent No.: US 6,605,093 B1
(45) Date of Patent: Aug. 12, 2003

(54) DEVICE AND METHOD FOR USE WITH AN OPHTHALMOLOGIC INSERTOR APPARATUS

(75) Inventor: Larry W. Blake, Coto de Caza, CA (US)

(73) Assignee: Tekia, Inc., Irvine, CA (US)

( * ) Notice: Subject to any disclaimer, the term of this patent is extended or adjusted under 35 U.S.C. 154(b) by 0 days.

(21) Appl. No.: 09/477,945

(22) Filed: Jan. 5, 2000

Related U.S. Application Data

(63) Continuation-in-part of application No. 09/061,652, filed on Apr. 17, 1998, now Pat. No. 6,280,449, which is a continuation-in-part of application No. 08/956,987, filed on Oct. 24, 1997, now abandoned.
(60) Provisional application No. 60/114,850, filed on Jan. 6, 1999.

(51) Int. Cl.[7] .................................................. A61F 9/00
(52) U.S. Cl. ...................................... 606/107; 623/6.12
(58) Field of Search ............................ 606/107, 1, 108, 606/191–213; 623/4, 6, 4.1, 6.11, 5.11, 6.12, 11.11; 604/19, 22

(56) References Cited

U.S. PATENT DOCUMENTS

| | | |
|---|---|---|
| 450,266 A | 4/1891 | Truax |
| 2,761,446 A | 9/1956 | Reed |
| 3,156,240 A | 11/1964 | Harrison et al. |
| 3,678,927 A | 7/1972 | Soichet |
| 3,703,174 A | 11/1972 | Smith |
| 3,757,781 A | 9/1973 | Smart |
| 3,791,689 A | 2/1974 | Boone et al. |
| 3,883,902 A | 5/1975 | Lynch |
| 4,251,887 A | 2/1981 | Anis |
| 4,303,268 A | 12/1981 | Davidson |
| 4,356,817 A | 11/1982 | McKibben et al. |
| 4,573,998 A | 3/1986 | Mazzocco |
| 4,681,102 A | 7/1987 | Bartell |
| 4,702,244 A | 10/1987 | Mazzocco |
| 4,715,373 A | 12/1987 | Mazzocco et al. |
| 4,747,404 A | 5/1988 | Jampel et al. |
| 4,759,359 A | 7/1988 | Willis et al. |
| 4,765,329 A | 8/1988 | Cumming et al. |
| 4,834,094 A | 5/1989 | Patton et al. |
| 4,836,201 A | 6/1989 | Patton et al. |
| 4,836,202 A | 6/1989 | Krasner |
| 4,862,885 A | 9/1989 | Cumming |
| 4,878,906 A | 11/1989 | Lindemann et al. |
| 4,919,130 A | 4/1990 | Stoy et al. |
| 4,934,363 A | 6/1990 | Smith et al. |
| 4,969,458 A | 11/1990 | Wiktor |

(List continued on next page.)

FOREIGN PATENT DOCUMENTS

| | | |
|---|---|---|
| DE | 42 36 210 C | 4/1994 |
| EP | 0 340 698 A | 8/1989 |
| EP | 0 340 698 A2 | 11/1989 |
| WO | WO 96/03924 A1 | 2/1996 |
| WO | WO 96/15743 | 5/1996 |
| WO | WO 96/28121 | 9/1996 |
| WO | WO 97/26844 | 7/1997 |
| WO | WO 98/12969 | 4/1998 |

*Primary Examiner*—Glenn K. Dawson
(74) *Attorney, Agent, or Firm*—Mueting, Raasch & Gebhardt, P.A.

(57) ABSTRACT

This invention discloses devices for use with an ophthalmologic insertor apparatus. In one embodiment, the device is a flexible, stretchable sleeve holder adapted to fit over a deformable sleeve that houses an implant. The sleeve holder facilitates loading of an implant into the sleeve by providing a suitable gripping surface. Application of a compressive force to the sleeve holder further allows the implant to be immobilized within the sleeve. After loading of the implant into the sleeve, the holder may be used as a collar or hub to secure the sleeve to an insertor hand-piece. Methods for loading implants into delivery sleeves, methods for attaching sleeves to inserters, and methods for delivering implants to an incision are also disclosed.

23 Claims, 18 Drawing Sheets

U.S. PATENT DOCUMENTS

| | | |
|---|---|---|
| 5,007,900 A | 4/1991 | Picha et al. |
| 5,007,913 A | 4/1991 | Dulebohn et al. |
| 5,066,297 A | 11/1991 | Cumming |
| 5,098,439 A | 3/1992 | Hill et al. |
| 5,100,410 A | 3/1992 | Dulebohn |
| 5,123,905 A | 6/1992 | Kelman |
| 5,171,241 A | 12/1992 | Buboltz et al. |
| 5,190,552 A | 3/1993 | Kelman |
| 5,190,553 A | 3/1993 | Kanert et al. |
| 5,275,604 A | 1/1994 | Rheinish et al. |
| 5,281,227 A | 1/1994 | Sussman |
| 5,292,324 A | 3/1994 | McDonald |
| 5,304,182 A | 4/1994 | Rheinish et al. |
| 5,312,413 A | 5/1994 | Eaton et al. |
| 5,354,333 A | 10/1994 | Kammann et al. |
| 5,395,378 A | 3/1995 | McDonald |
| 5,425,734 A | 6/1995 | Blake |
| 5,456,687 A | 10/1995 | DeVenuto |
| 5,468,246 A | 11/1995 | Blake |
| 5,474,562 A | 12/1995 | Orchowski et al. |
| 5,494,484 A | 2/1996 | Feingold |
| 5,496,328 A | 3/1996 | Nakajima et al. |
| 5,499,987 A | 3/1996 | Feingold |
| 5,549,614 A | 8/1996 | Tunis |
| 5,556,400 A | 9/1996 | Tunis |
| 5,562,676 A | 10/1996 | Brady et al. |
| 5,571,112 A | 11/1996 | DeVenuto |
| 5,578,020 A | 11/1996 | Mosley |
| 5,578,042 A | 11/1996 | Cumming |
| 5,582,613 A | 12/1996 | Brady et al. |
| 5,582,614 A | 12/1996 | Feingold |
| 5,607,433 A | 3/1997 | Polla et al. |
| 5,616,148 A | 4/1997 | Eagles et al. |
| 5,620,450 A | 4/1997 | Eagles et al. |
| 5,653,715 A | 8/1997 | Reich et al. |
| 5,792,119 A | 8/1998 | Marx |
| 5,919,197 A | 7/1999 | McDonald |
| 6,280,449 B1 * | 8/2001 | Blake .................. 606/107 |

* cited by examiner

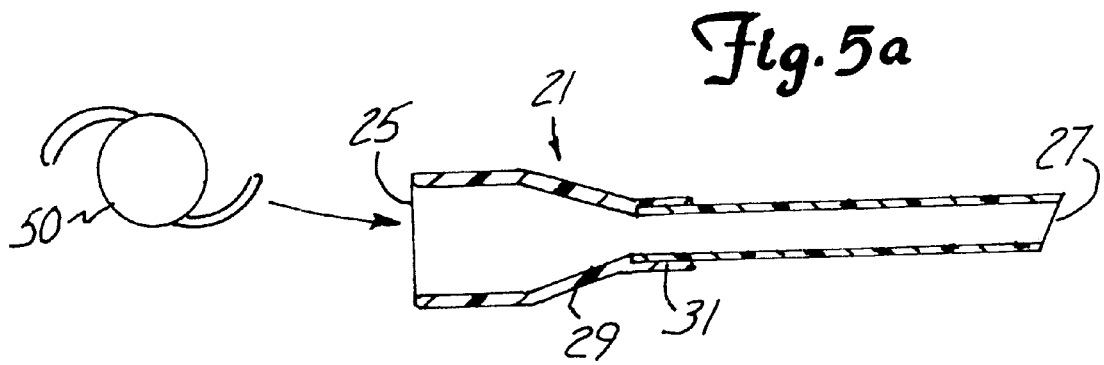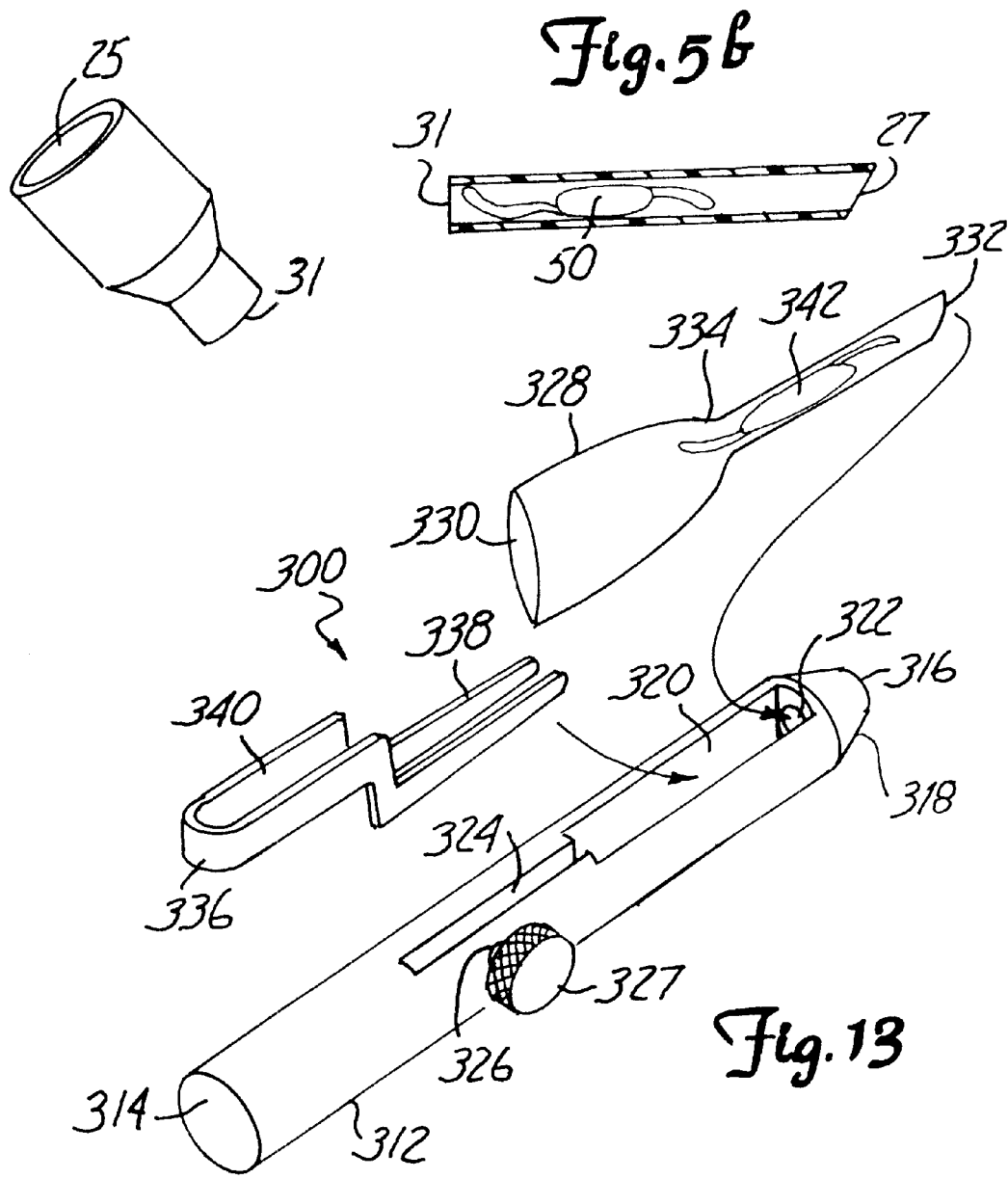

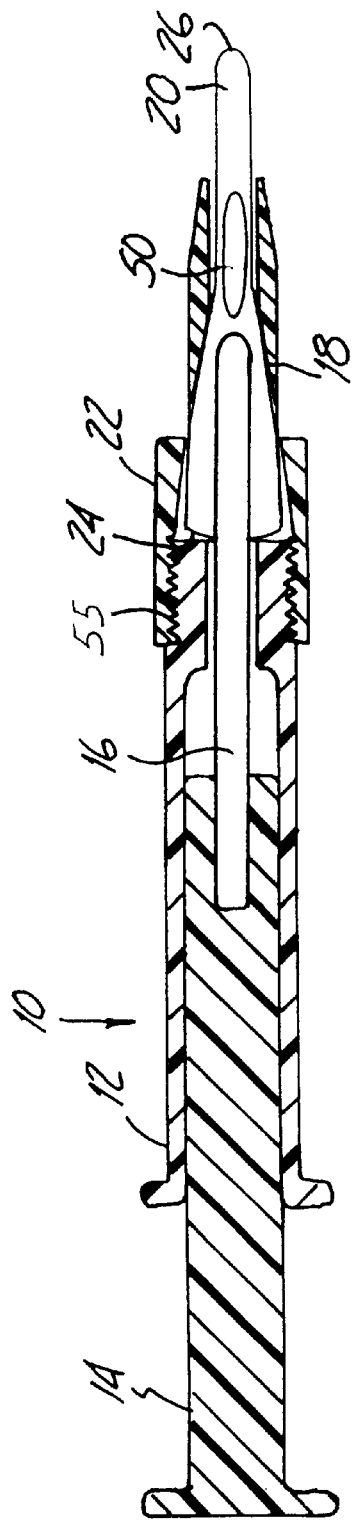
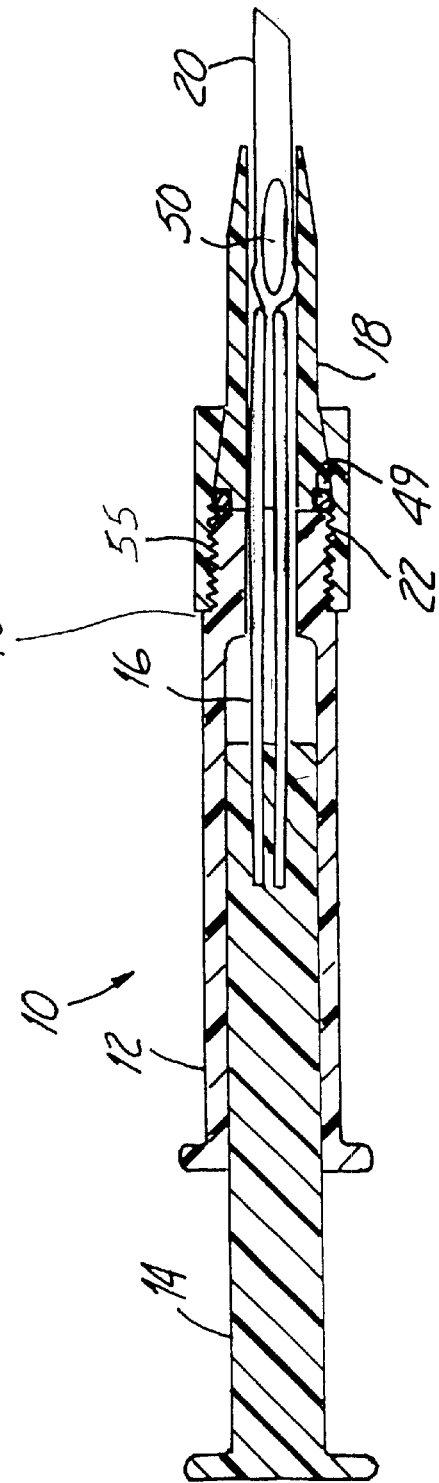
Fig. 6
Fig. 7

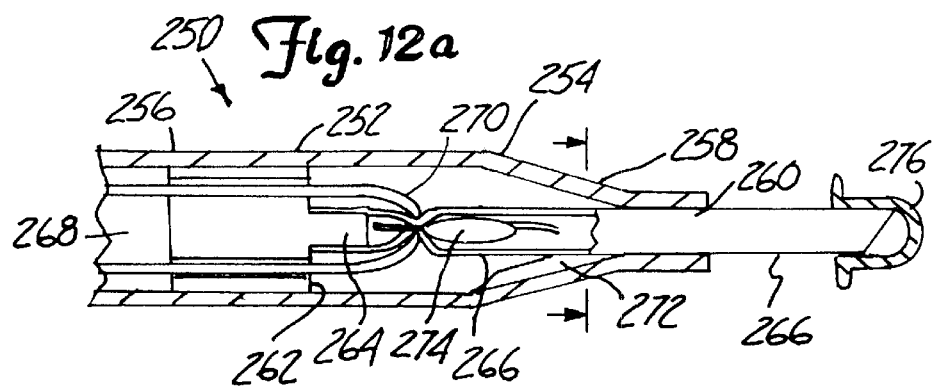
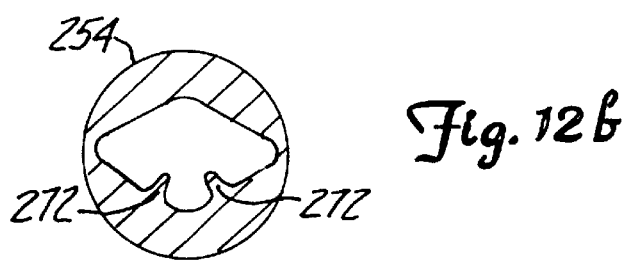
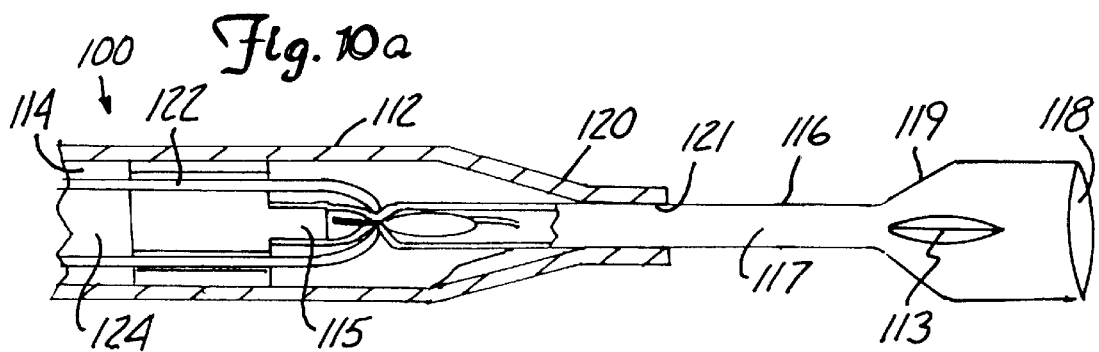
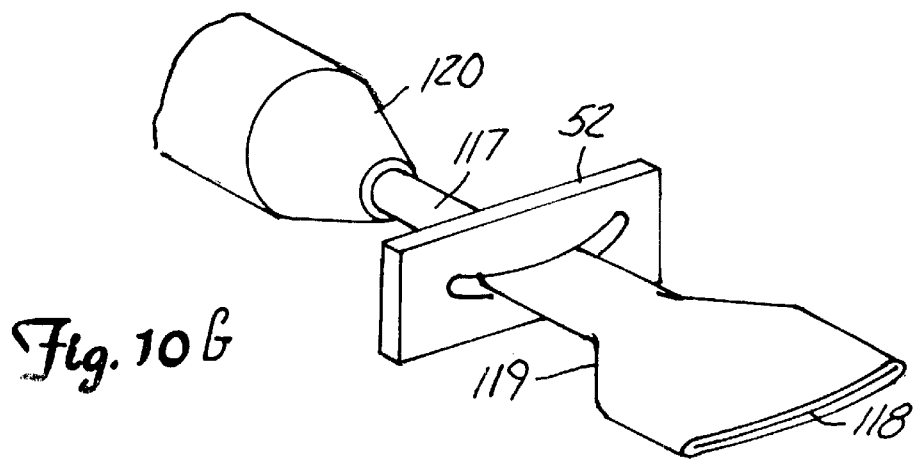

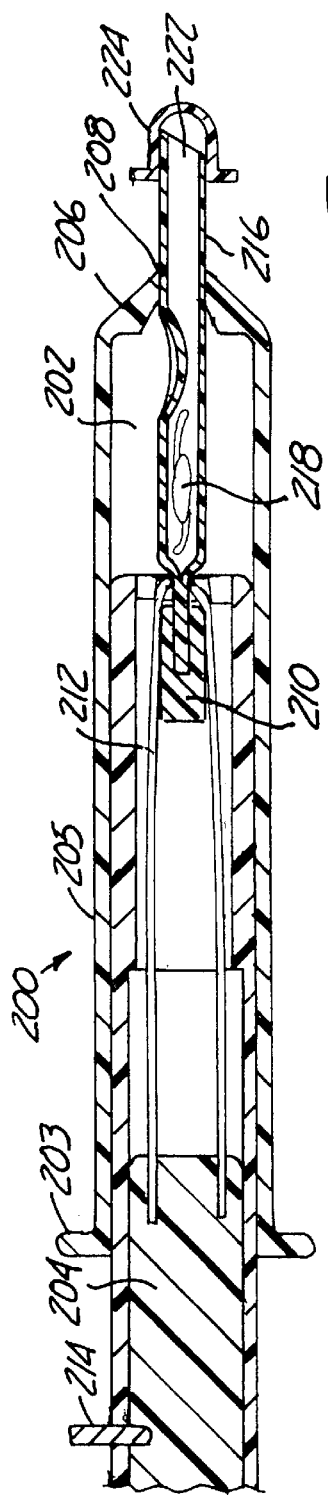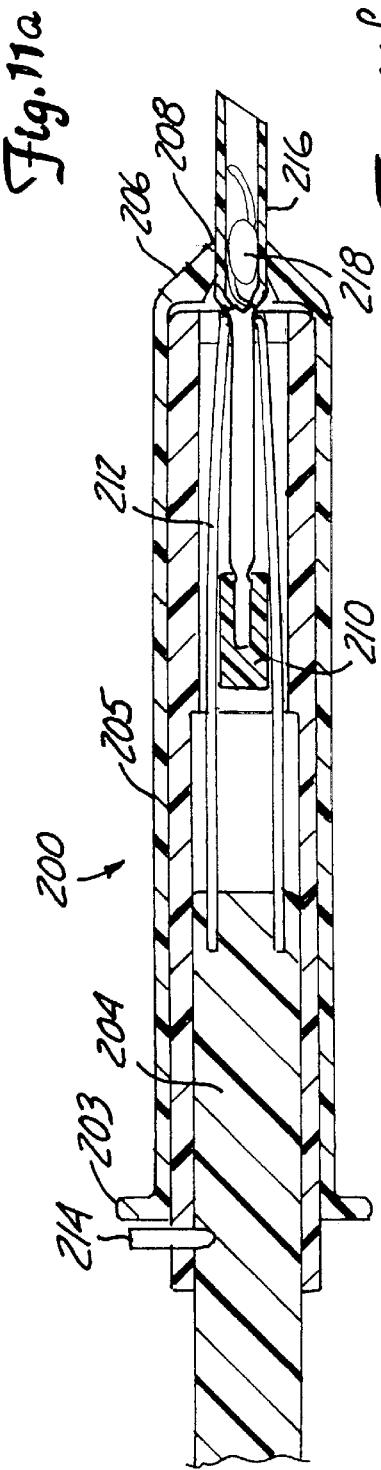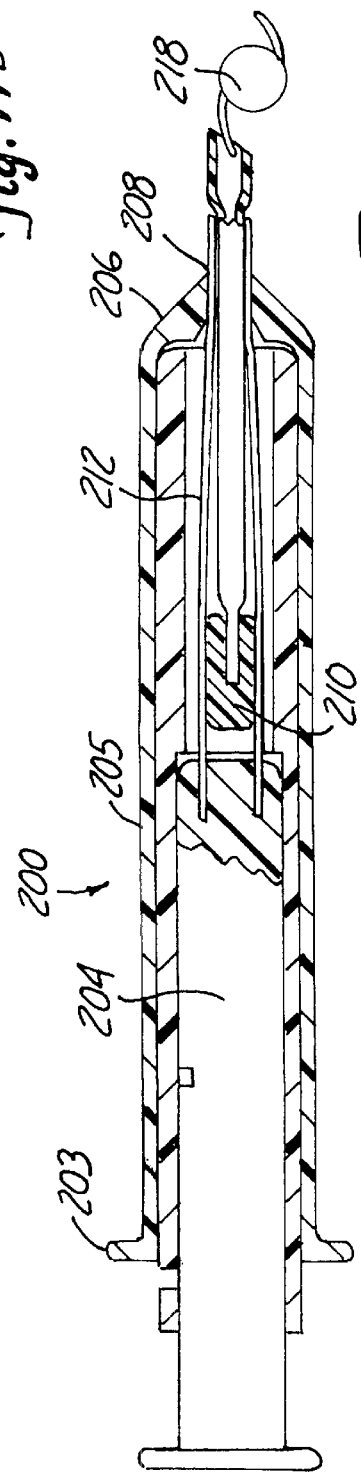

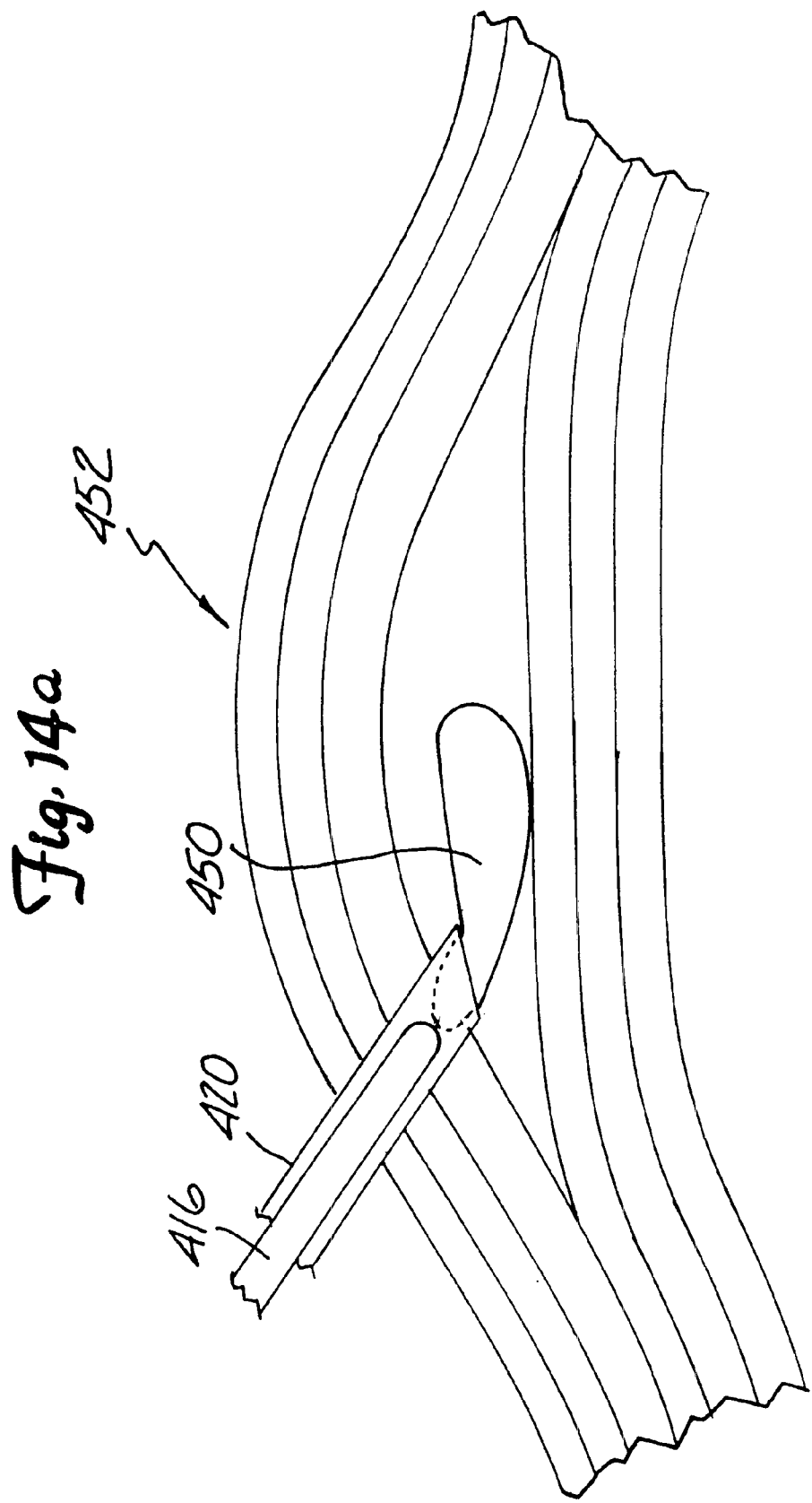

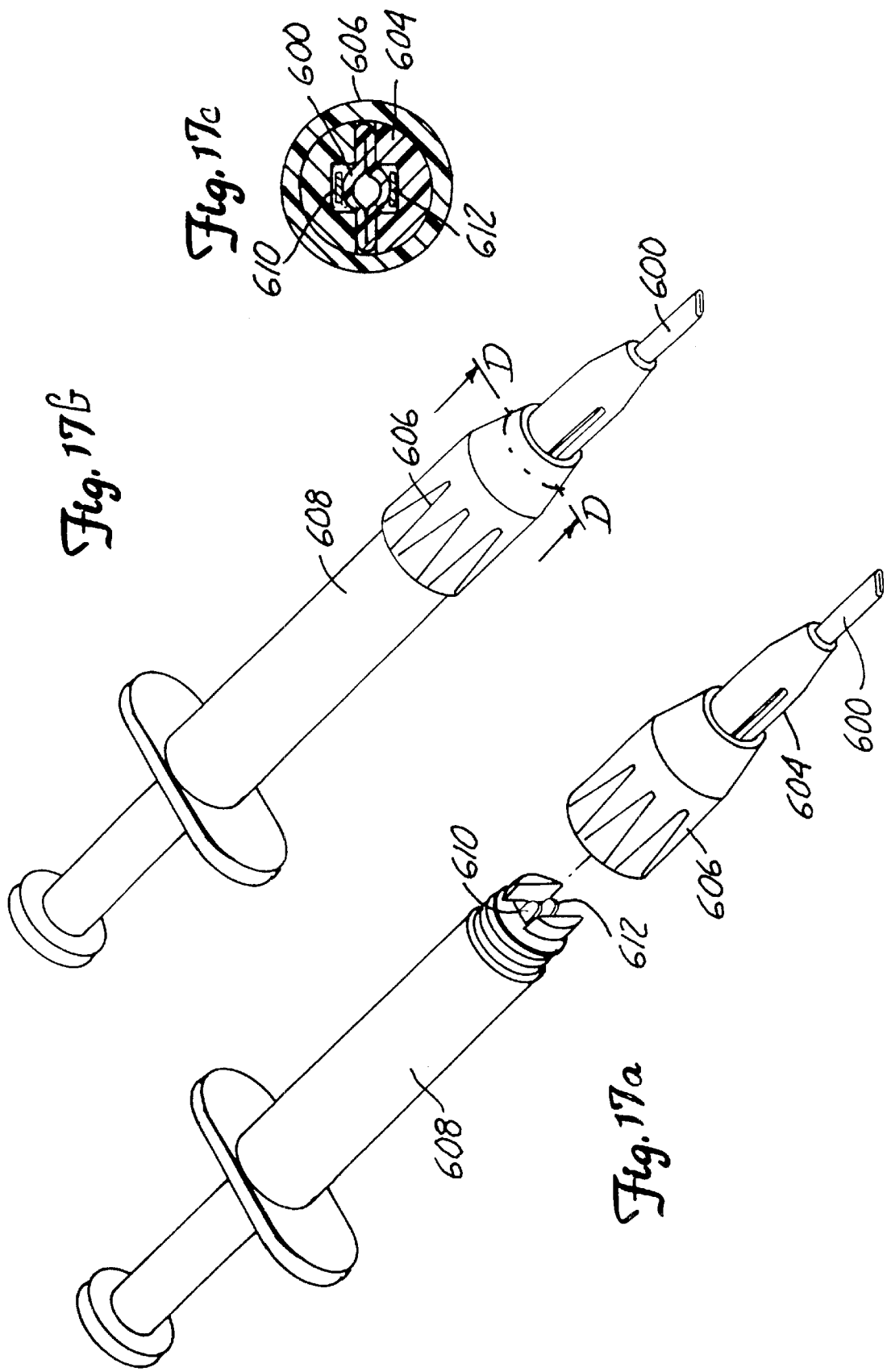

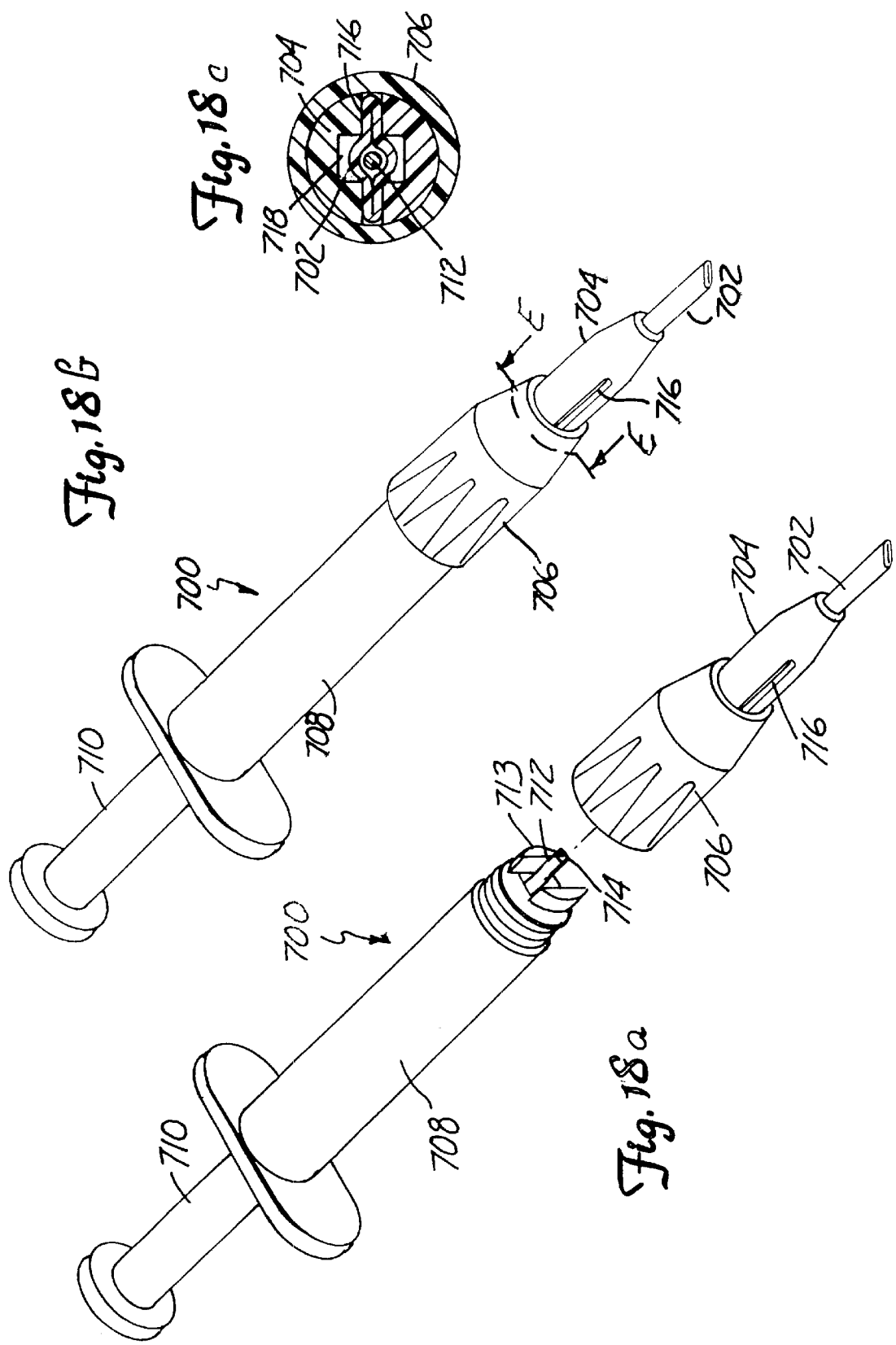

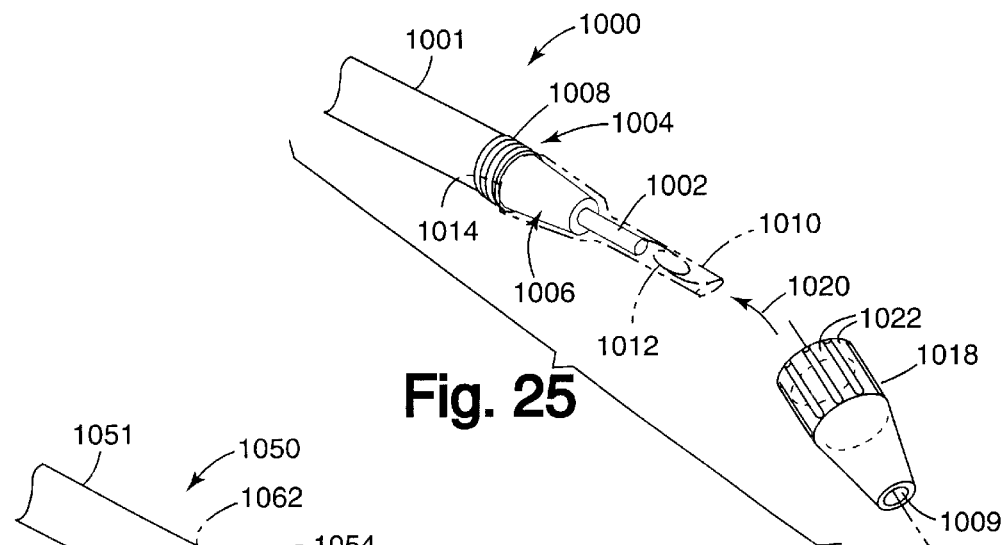
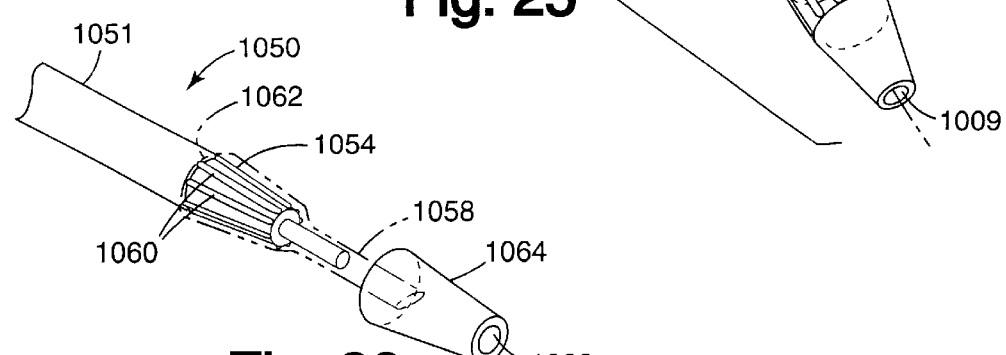
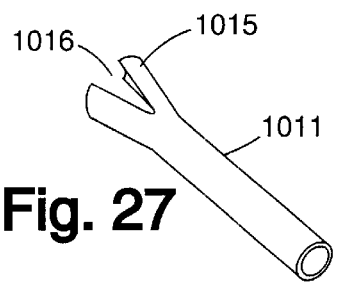
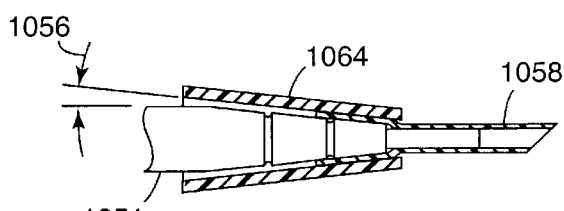
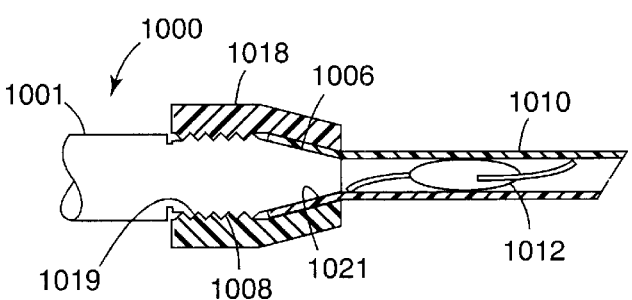

DEVICE AND METHOD FOR USE WITH AN OPHTHALMOLOGIC INSERTOR APPARATUS

RELATED APPLICATIONS

This application is a C/P of U.S. patent application Ser. No. 09/061,652 filed on Apr. 17, 1998, now U.S. Pat. No. 6,280,449, which is a continuation-in-part of U.S. patent application Ser. No. 08/956,987 filed on Oct. 24, 1997 now abandoned. This application further claims the benefit of U.S. Provisional patent application. Ser. No. 60/114,850 filed on Jan. 6, 1999. These applications are hereby incorporated by reference in their respective entireties.

FIELD OF THE INVENTION

The present invention relates to the field of implantation methods. Preferably, the invention relates to the field of ophthalmology and to the use of medical devices in ophthalmologic surgery. In a particularly preferred embodiment, the present invention relates to methods and procedures for inserting implants into the eye.

BACKGROUND OF THE INVENTION

Artificial intraocular lenses are widely used to replace the human crystalline lens of the eye. The human crystalline lens is a living transparent structure composed primarily of protein having a thickness of about five millimeters and a diameter of about nine millimeters. The lens is suspended behind the iris by zonula fibers that connect the lens to the ciliary body. A lens capsule surrounds the lens; the front portion of the capsule generally referred to as the anterior capsule and the back portion generally referred to as the posterior capsule.

The term "cataract" refers to the opacity of the lens of the eye. There are a variety of types of cataracts and for most cataracts, surgical intervention is required to remove and replace the lens with an artificial intraocular lens.

The transparency of the lens depends on the physiochemical state of the lens proteins. These proteins, like the proteins of other organs, are sensitive to changes in the properties of their surrounding fluid. Changes in the concentration of dissolved salts, in the osmotic pressure, in the pH or in the enzyme activity of the surrounding fluid can alter the properties of the lens proteins. Also, like other organs, changes to the proteins of the lens occur with age. A common type of cataract that occurs in elderly people is known as a senile cataract. This type of cataract has no known etiology and none of the forms of cataract produced experimentally to date closely resemble the senile cataract.

Artificial intraocular lenses generally comprise an optical region and a support, or haptic, to facilitate positioning and centering of the intraocular lens within the eye. Intraocular lenses have been made from a number of different materials. For example, hard lenses have been prepared from polymethylmethacrylate (PMMA) and optical glass while flexible lenses have been prepared from silicone, poly HEMA (polyhydroxyethylmethymethacrylate), acrylics, collagen, and combinations thereof. Flexible lenses have the advantage that they can be folded or otherwise deformed prior to implantation to reduce the overall size of the lens during the artificial lens implantation procedure.

There are a number of procedures and devices that have been developed for the removal of the natural lens followed by the insertion of an artificial lens. The extraction procedure can generally be categorized as intracapsular (i.e., where the lens is removed together with the lens capsule) or extracapsular (such as where a portion of the anterior capsule is circularly removed (capsulorhexis) and the posterior capsule is left intact).

Presently, phacoemulsification is a widely used method for the removal of diseased or damaged natural lens tissue. The phacoemulsification process generally employs a small incision typically of about 2 millimeters (mm) to about 4 mm in length (but potentially as small as 1 mm) through the cornea and a probe is used to ultrasonically break apart and remove the crystalline lens through the capsulorhexis.

There are a number of intraocular lens injectors that have been described in the literature to position a deformable artificial intraocular lens in the eye. These injectors use an incision of about 2 mm to about 4 mm, the incision size most frequently used in most phacoemulsification procedures. A larger (about 4 mm to about 5 mm) capsulorhexis incision, also used in phacoemulsification procedures, is used to position the lens without requiring elongation of the incision during the injection process.

U.S. Pat. No. 4,681,102 to Bartell discloses one type of device to implant an intraocular lens through a small incision. The injector comprises a load chamber that is used to fold a soft intraocular lens into a shape having a smaller cross-sectional area than the original unfolded cross-sectional dimension of the lens. The load chamber comprises two hinged members that together define a generally cylindrical lumen. Each of the two members includes a flange that extends non-parallel to cylindrical members at a point of connection and permits manipulation of the cylindrical members from a first open position to a second closed position. The intraocular lens is inserted into the load chamber when the two members are in an open position. The flanges are advanced towards each other causing the two members to form the generally cylindrical chamber. As the two members advance towards each other, the intraocular lens that is inserted in the chamber is compressed to conform to the generally cylindrical shape of the members in the closed position. This device and those devices that include a rigid chamber for deforming the lens can damage the lens during the deformation process if the lens is not accurately and carefully positioned in the chamber.

A number of patents use a push-rod (also described in these patents as a pusher or piston-type device) to apply a force directly on a lens and to push the deformed lens from the device into the eye. For example, the loading chamber of Bartell (supra) is placed into a rigid injector portion fitted with a push-rod. The push-rod pushes the intraocular lens through a generally circular lumen of the loading chamber and into an injector nozzle. The pushing action of the push-rod can further damage the lens material and haptics before the lens is positioned in the eye.

U.S. Pat. Nos. 4,702,244 and 4,573,998 to Mazzocco discloses a push-rod type of device that functions similar to a plunger of a syringe to provide a hydraulic force on a lens. The device includes a chamber for containing the intraocular lens in an unstressed state and for orienting the lens in a prescribed orientation to facilitate lens placement within the eye. The plunger is used to exert a direct force on the lens or a direct force on liquid surrounding the lens, sufficient to deform the lens such that the optical zone is deformed to a substantially smaller cross-sectional diameter than the optical zone in an unstressed state. The device includes a means to expel the lens from the device for placement in the eye. The surgical device disclosed by Mazzocco requires the use of a direct force such as a hydraulic force or a pneumatic force to move the lens from its unstressed stated into a deformed position. In the embodiment that compresses the lens from an unstressed state to a stressed state, the lens is propelled toward a small opening at the end of a holding tube. As the lens approaches the opening it is folded back against itself and compressed to fit through the opening. The orientation of the lens in the device is not uniform, nor would deformation be consistent with each injection. Moreover, the hydraulic force would likely be quite high and this pressure is likely not practical for use in the internal aspects of the eye.

U.S. Pat. No. 5,468,246 to Blake discloses another type of intraocular lens injector that compresses the diameter of the intraocular lens by rolling the lens into a tight cylindrical tube that can be inserted into the eye through a small incision of about 2 millimeters to about 4 millimeters. This device also uses a push-rod-type device to apply a direct force to move the lens from the injector device into the eye.

U.S. Pat. No. 5,562,676 to Brady, U.S. Pat. No. 5,275,604 to Rheinish, U.S. Pat. No. 5,474,562 to Orchowski, U.S. Pat. No. 4,919,130 to Stoy, U.S. Pat. No. 5,123,905 to Kelman and U.S. Pat. No. 5,616,148 to Eagles use an injector with a tapered or conical loading chamber to guide and fold the lens into a rigid lumen. These patents also use a push-rod to inject the lens from the lumen into the eye. A problem with these injectors is that the internally positioned push-rod is in direct contact with the lens assembly. This direct contact can result in distortion, bending or breakage of a trailing haptic. In addition, compressive forces on soft or fragile lens materials can tear the lens or destroy a haptic. In addition, during compression, the push-rod can catch or wedge a portion of the lens between the rigid lumen of the device and the push-rod mechanism.

There remains a need for a device for introducing a flexible implant, particularly fragile foldable lenses into the body without damaging that implant. In particular, there is a need for a device to implant a foldable intraocular lens into an eye without damaging the lens or the haptics during the implantation process.

SUMMARY OF THE INVENTION

This invention discloses insertor devices that employ a flexible compressible sleeve to deliver an implant into the body. In accordance with one embodiment of the invention, the invention relates to a sleeve supporting device comprising a substantially flexible hub having a first opening and a second opening and a lumen extending therethrough. The lumen is adapted to substantially conform to the shape of a sleeve.

In another embodiment, the invention relates to a device for loading an implant into an implant delivery apparatus. The device comprises an elastomeric holder having an exterior surface and an interior surface. The exterior surface is suitable for gripping and the interior surface is adapted to generally receive and conform to an exterior shape of the implant delivery apparatus.

In another aspect of this invention, the invention relates to a method for assembling an implant insertion device. The method comprises loading an implant into a sleeve where the sleeve has a first opening and a second opening. The method further comprises coupling the first opening of the sleeve to a first end of a hand-piece and securing the sleeve to the first end of the hand-piece with a deformable sleeve holder.

In yet another aspect, the invention relates to a system for loading an implant. The system comprises a flexible, compressible sleeve wherein the sleeve comprises a first opening and a second opening and a first lumen extending through the sleeve and further wherein the sleeve is prepared from a non-opaque material. The width of the first opening is larger than the width of the second opening. The system further comprises a sleeve holder prepared from a substantially flexible material and comprising a second lumen extending therethrough, wherein the second lumen is adapted to substantially conform to the shape of the sleeve.

In still another aspect of the invention, a system for introducing an implant into the body is provided comprising a flexible, compressible sleeve. The sleeve comprises a first opening and a second opening and a first lumen extending through the sleeve, wherein the sleeve is prepared from a non-opaque material. The width of the first opening is larger than the width of the second opening. The system further comprises a sleeve holder prepared from a substantially flexible material and comprising a second lumen extending therethrough, wherein the second lumen is adapted to substantially conform to the shape of the sleeve. An implant positioned within the first lumen is also included. In yet another aspect of the invention, a hand-piece having a first end is also included. The hand-piece is capable of coupling to and retaining the sleeve. In yet another configuration, the first end of the hand-piece comprises at least one circumferential barb.

In still yet another embodiment of the invention, the invention relates to a kit. The kit includes a flexible, compressible sleeve wherein the sleeve comprises a first opening and a second opening and a first lumen extending through the sleeve, where the sleeve is prepared from a non-opaque material. The width of the first opening is larger than the width of the second opening. The kit further comprises a sleeve holder prepared from a substantially elastomeric material and comprising a second lumen extending therethrough. The second lumen is adapted to receive and substantially conform to the shape of the sleeve. The kit further comprises an implant positioned within the first lumen and a hand-piece having a first end, the first end adapted to couple with the first opening of the sleeve.

Other embodiments are also possible without departing from the scope of the invention. Advantageously, the present invention provides devices and methods for use with an ophthalmologic insertor apparatus, various embodiments of which are described and illustrated below.

BRIEF DESCRIPTION OF THE DRAWINGS

FIG. 1a is a side view of a collet and FIG. 1b is a cross-section through the collet at G—G as illustrated in FIG. 1.

FIG. 3a illustrates a circular cross-section; FIG. 3b, an elliptical cross-section; FIG. 3c, a flattened cross-section; FIG. 3d, an enveloped cross-section; FIG. 3e, a pleated cross-section; FIG. 3f, a plurality of pleats in cross-section; and FIG. 3g, a "V" shaped cross-section.

FIGS. 4a through 4f are cross-sectional views of the distal portion of a collet from the device of FIG. 1. FIG. 4a illustrates a round configuration; FIG. 4b, a rhomboid configuration; FIG. 4c, a winged circular configuration; FIG. 4d, an expanded winged circular configuration; FIG. 4e, another embodiment of an expanded winged circular configuration; and FIG. 4f, a scrolled configuration.

FIG. 5a is a cross-sectional view of a multi-piece sleeve according to this invention. FIG. 5b illustrates a multi-piece sleeve following separation of the sleeve.

FIG. 6 is a cross-sectional view of an assembled insertor device according to FIG. 1.

FIG. 7 is a cross-sectional view of the assembled insertor device of FIG. 6 rotated 90°.

FIG. 10a is a cross-section of a front-loading device according to this invention with a front-loading sleeve. FIG. 10b is a view of the front loading device with a squeezing tool.

FIGS. 11a through 11c illustrate a preassembled insertor according to the present invention having a multi-step pushing mechanism. FIG. 11a illustrates the preassembled insertor. FIG. 11b illustrates a first step in the pushing mechanism and FIG. 11c illustrates a second step in the pushing mechanism.

FIG. 12a is another embodiment of a lens insertor of this invention illustrating external bending guides. FIG. 12b provides a cross-section through the insertor of FIG. 12a to illustrate the external bending guides.

FIG. 13 is another embodiment of an insertor according to this invention.

FIG. 14a is a cross-sectional view of the eye with a device according to this invention inserting a foldable intraocular lens.

FIG. 17a is a perspective view of an assembled sleeve, collet and ring clamp positioned onto a hand-piece with blades. FIG. 17b is a perspective view of the assembled device of FIG. 17a. FIG. 17c is a cross-section through lines D—D illustrating the position of blades around the sleeve within the lumen of the collet.

FIG. 18a is a perspective view of an assembled sleeve, collet and ring clamp positioned onto a hand-piece with a push-rod. FIG. 18b is a perspective view of the assembled device of FIG. 18a. FIG. 18c is a cross-section through lines E—E illustrating the position of the push-rod in the sleeve within the lumen of the collet.

FIG. 25 is a perspective view of a sleeve with an intraocular lens therein for attachment to an insertor in accordance with yet another embodiment of the invention.

FIG. 26 is a perspective view of a sleeve with an intraocular lens therein for attachment to an insertor in accordance with still yet another embodiment of the invention.

FIG. 27 is a perspective view of a sleeve having expansion slits in accordance with one embodiment of the invention.

FIG. 28 is a cross-sectional view of the assembled sleeve and insertor in accordance with another embodiment of the invention.

FIG. 29 is a cross-sectional view of the assembled sleeve and insertor of FIG. 25.

DETAILED DESCRIPTION OF THE PREFERRED EMBODIMENTS

Figure 1:
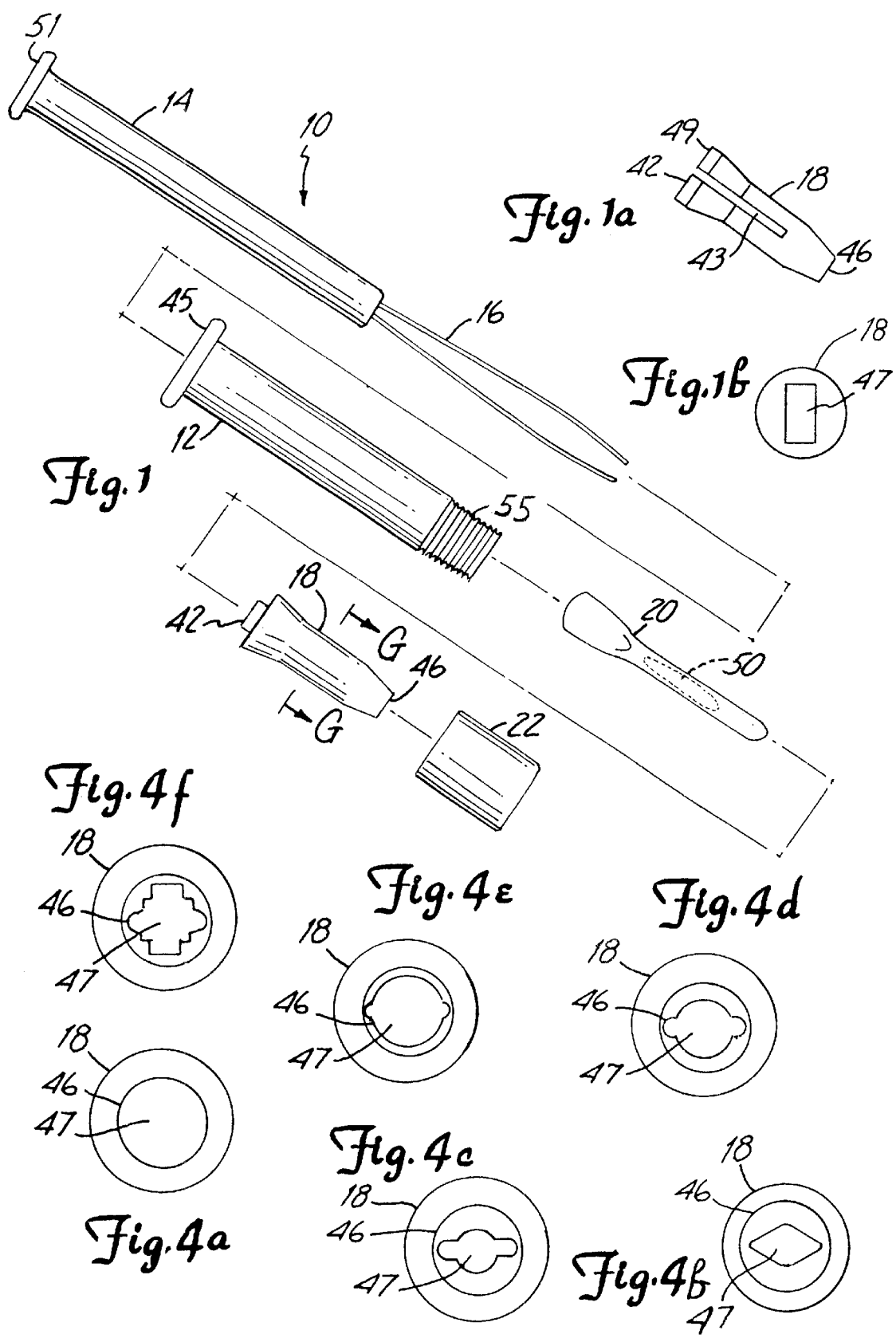
FIG. 1 is an exploded perspective view of a preferred lens insertor of the present invention.

The present invention provides a novel device for the introduction of a variety of implantable devices, preferably lenses, such as an intraocular lens, into the eye. The invention also relates to the use of a flexible and distendable sleeve to house a flexible implant during introduction of the implant into the body. In contrast to other implantation devices currently available, one embodiment of this invention applies off-axis an external squeezing force on a flexible, distendable sleeve containing an implant to gently urge the implant through the sleeve, from the device and into the body. Other devices for the implantation of intraocular lenses currently apply a direct force such as through a compressive push-rod, also referred to as a pusher or piston, that directly contacts the lens to inject the lens into the eye. In a preferred application of the present invention, the device is useful for the introduction of a lens into the eye and in particular, for the introduction of an intraocular lens through an incision in the ocular tissue, such as the incisions employed using a phacoemulsification cataract removal procedure.

The devices of this invention are insertion devices. That is, the term "insertor" is used herein to refer to a device that places an implant into a passageway, cavity or tissue of the body. In one embodiment of this invention, the insertors of this invention use an off-axis or indirect force to advance the implant into the body.

The devices of this invention are useful for inserting a variety of items in the eye. For example, in a preferred device, the device is used to insert an intraocular lens into the eye. Modifications of the device permit the design of a variety of devices suited for insertion of a variety of lenses or implants into the eye including, but not limited to, a posterior and anterior intraocular lens, a corneal inlay lens inserted into the cornea of the eye, either as an inlay or as a corneal refractive implantable contact lens (ICL), a scleral buckle implant, to introduce a contact lens onto the eye, to introduce an artificial duct or implant material including tubing, and the like into the eye to shunt fluid from the anterior chamber of the eye such as for glaucoma surgery. The devices of this invention can be used to position an implant elsewhere in the body. For example, to introduce subcutaneous or intramuscular implants, including sustained drug release devices, or as catheter-like devices, and the like. While the present invention is described by way of its ability to introduce an intraocular lens or other lenses into an eye, those of ordinary skill in the art will recognize that a variety of implantable items can be introduced into a variety of positions in the body through devices as described in this invention.

The term "proximal" is used herein to refer to that portion of the device or element of the device that is closest to the physician's finger that is being used to activate the pusher element of the devices of this invention. The term "distal" is used herein to refer to that portion of the device or element of the device that is farthest from the physician's finger that is being used to activate the pusher element of the devices of this invention.

The term "squeezing" is used herein to refer to a compressive off-axis force applied behind an object to mobilize the object ahead of the off-axis force along a defined course. The compressible force includes a component transverse to the longitudinal axis of the device, where the longitudinal axis is defined by the direction of movement of the implant being inserted.

The term "soft implant" is used herein to refer to a malleable, ductile, compressible elastic, rubbery or gelatinous substance having a reading on an A durometer of generally about 20 A to about 70A, but could be as low as 5 A for a hydrophillic contact lens or about 90 A for a flexible acrylic material.

Durometer instruments are available from Pacific Transducer Corp., Los Angeles, Calif.

The term "flexible and compressible" sleeve refers to sleeves prepared from a variety of flexible materials, including flexible polymeric materials, such as those that can be generally measured on a D scale or an A scale, and preferably materials having a D durometer reading from about 40 D to about 80 D. Other hardness scales can also be used. In general, durometer testers and their methods of use are described in ASTM D-2240. The "A" scale can be used, for example, to measure the flexibility or relative hardness of synthetic rubbers, neoprene, silicones, felt, and the like. The "B" scale can be used to measure the flexibility or alternatively the relative hardness of a variety of rubbers and elastomers. The "C" scale is used to measure medium hard rubbers and plastics. The "D" scale is used to measure a variety of plastics, plexiglass, polystyrene, vinyls, and the like. The "OO" scale can be used to measure the hardness of materials such as sponges, rubber or soft rubber. Those of ordinary skill in the art will recognize that the materials need be readily compressible by the blades of the devices of this invention and therefore, a variety of materials used to construct objects to be inserted as an implant are considered "flexible and compressible" and preferably malleable for purposes of this disclosure, particularly in view of exemplary sleeve materials supplied later in this disclosure.

The term "pleat" as used in this invention refers to one or more folds or creases present in all or a portion, preferably at least the tapered portion, of a sleeve of this invention.

FIG. 1 is a preferred embodiment of the present invention for inserting a lens into the eye of a patient. The exploded view of insertor 10 provides a hand-piece 12, including a pusher element 14 capable of engaging at least one push-blade 16, a collet 18 capable of receiving a compressible sleeve 20 and a ring clamp 22 to secure the collet 18 to hand-piece 12.

Sleeve 20 is prepared from a compressible, flexible, deformable and smooth material, preferably a flexible polymeric material such as ethylene tetrafluoroethylene (ETFE, Zeus Corp. Orangeburg. S.C.), but other materials can be used, including, but not limited to: other tetrafluoroethylenes (e.g., polytetrafluoroethylene (PTFE), fluorinated ethylenepropylene, perfluoro-alkoxyfluorocarbons, flexible vinyls (e.g., polyvinyl chloride or polyvinylide fluoride), polyimide, polyamide, polyester, silicones, polyolefin materials, non-opaque TEFLON, polyvinyl chloride with a hardness range of about 35D to about 80D, etc. Preferred materials are sufficiently non-opaque that an implant can be seen in the sleeve when positioned therein. Sleeve 20 is preferably formed from a flexible, deformable and compressible tubing (e.g., ETFE or PTFE tubing) that is preferably malleable and capable of being pressed or distended. Alternatively, the sleeve can be injection molded. The sleeve 20 can be coated on its interior or exterior surfaces with a variety of friction reducing materials to ease the passage of a lens through the length of the sleeve 20. The coatings can, for example, reduce friction on the lens by the sleeve. Preferred coating materials include, but are not limited to, silicones, such as HYDRO-SIL (TUA Systems, Sarasota, Fla.), ion -exchange hydrophilic treatments such as HYDRO-SILK or other coatings including, but not limited to, heparin, PARYLENE (Nova Tran Corp., Clear Lake, Wis.), or NOVA TRAN (Nova Tran Corp), etc.

Figure 2:
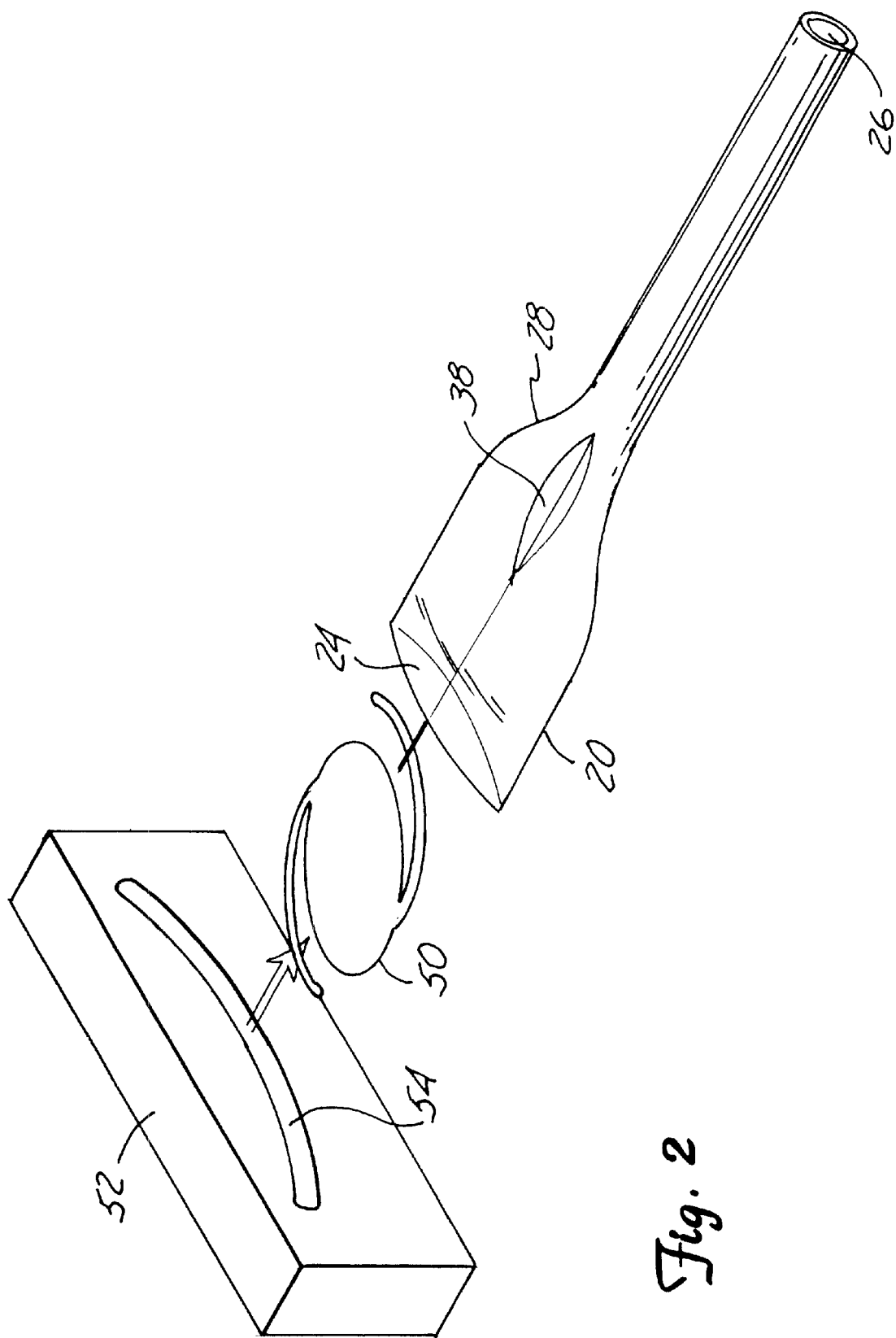
FIG. 2 illustrates a preferred sleeve embodiment and a squeezing tool according to this invention.

Referring now to FIG. 2, sleeve 20 preferably includes a first opening 24 capable of receiving an intraocular lens. In one embodiment, first opening 24 (proximal portion of sleeve) has a width that is sufficient to receive an unfolded or substantially unfolded lens; however the first opening 24 can be small enough to require some deformation of the lens. Typically for intraocular lens implantation, first opening 24 is preferably at least about 1.5 millimeters (mm) in width and preferably less than about 10 mm in width and preferably for an intraocular lens insertor, greater than about 3 mm and less than about 9 mm in width. The walls of the material used to prepare sleeve 20 can be a variety of thicknesses provided that the sleeve 20 remains readily compressible by, for example, blades 16, maintains its integrity during use and is sufficiently deformable to permit positioning of an intraocular lens within the sleeve.

The first opening 24 of the sleeve can have any of a variety of configurations including, but not limited to, straight edges, such as provided in FIG. 2, chamfered edges, curved edges, either concave or convex curves relative to the tip of the sleeve. Alternatively, the first opening 24 of the sleeve can be angled.

Sleeve 20 also includes a second opening 26 in the tubular portion of the sleeve and the width of sleeve 20 preferably decreases over at least a portion of the sleeve from first opening 24 to second opening 26 to provide a tapered portion 28 to sleeve 20. In a preferred embodiment, the taper of sleeve 20 preferably reduces the dimension of the sleeve from the first opening 24 to the second opening 26 within one-half of the length of the sleeve. The tapered portion 28 reduces the width of the sleeve toward the distal portion of the sleeve. For the intraocular lens embodiment, second opening 26 is at least about 1 mm in diameter and preferably less than about 4 mm in diameter with preferred dimensions for an intraocular lens insertor of between about 2 mm to about 2.5 mm for soft flexible lenses and as much as 4 mm for less flexible lenses such as acrylic lenses.

Preferably, the length of sleeve 20 is preferably at least about 1 cm and more preferably at least about 2 cm, for the intraocular lens embodiment, the sleeve is at least about 5 cm and typically, the sleeve 20 will be less than about 10 cm in length. In a preferred embodiment of an intraocular lens insertor, the length of sleeve 20 is preferably greater than about 2.5 cm and less than about 3 cm. For the front loading device, discussed below, the sleeve can be about 5 cm. Although longer or shorter sleeve lengths can be adapted to longer or shorter devices. Second opening 26 is preferably beveled, from about 16° to about 75° much like the tip of a needle to ease insertion of the implant into the eye, although a variety of configurations to second opening 26 are possible. The second opening 26 of sleeve 20 can take on a variety of other shapes and in one embodiment the second opening 26 is ellipsoid or circular in cross-section. Optionally, second opening 26 of sleeve 20 can be tapered or can be flared.

Figure 3A:
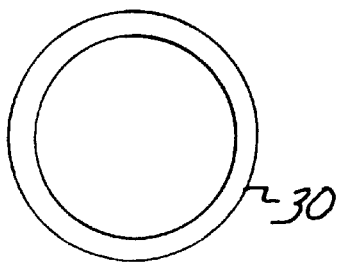
FIGS. 3a through 3g illustrate a series of cross-sectional configurations of at least the tapered portion of the sleeve of this invention.
Figure 3B:
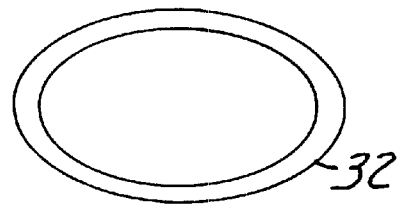
Figure 3C:
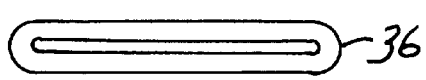
Figure 3D:
Figure 3E:
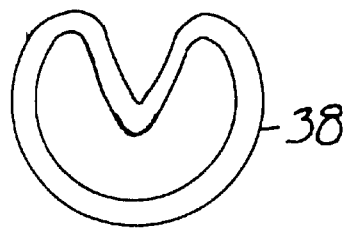
Figure 3F:
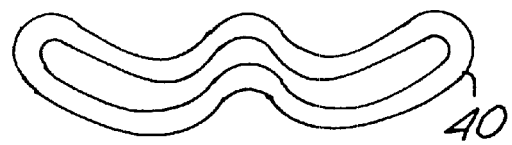
Figure 3G:
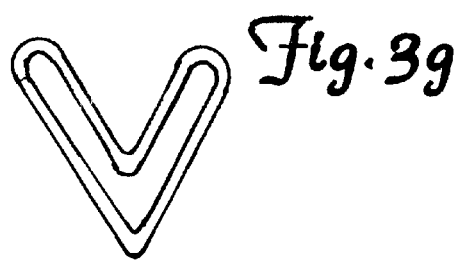

As shown in FIG. 3 (note that drawings having multiple views; e.g., FIG. 3a . . . FIG. 3g, may be referred to collectively by drawing number; e.g., FIG. 3), the cross-section of the sleeve 20 can have a variety of configurations. In a preferred embodiment, the tapered portion 28 of sleeve 20 can have any one of the configurations provided in FIG. 3. FIG. 3a illustrates a circular cross-section 30; FIG. 3b, an elliptical cross-section 32; FIG. 3c, a flattened cross-section 36; FIG. 3d, an enveloped cross-section 34; FIG. 3e, a pleated cross-section 38; FIG. 3f, a plurality of pleats in cross-section 40; FIG. 3g a "V" shaped configuration in cross-section, or a combination thereof. Those skilled in the art will appreciate that there are a number of other cross-sectional configurations that are possible.

In one embodiment, the tapered portion 28 of sleeve 20 is pleated 38 (see FIG. 2) for at least a portion of its length and preferably the tapered portion 28 of sleeve 20 is pleated while the distal portion of sleeve 20 is generally circular in cross-section but could be ovoid or flattened. The cross-sectional configurations of the sleeve 20 can serve as guides to promote folding of the implant, such as a lens in a sleeve. In addition, the shape of the sleeve 20 at the first opening 24 of the sleeve can vary and could be flattened, ellipsoid, ovoid, enveloped, pleated, or the like. Moreover, the cross-sectional configuration of sleeve 20 can vary from first opening 24 through tapered portion 28 to second opening 26. For example, the cross-section at first opening 24 can be ovoid, while the tapered portion is pleated and the portion of the sleeve adjacent to second opening 26 can be circular in cross-section. Pleats are not necessary and in the embodiments using a sleeve holder (infra), pleats are optional.

Sleeve 20 of FIG. 2 is illustrated as a single piece sleeve, that is a completely integral object. However, it is also contemplated that the sleeve 20 can be constructed from two or more pieces to form a multi-piece sleeve. FIGS. 5a and 5b illustrate a preferred embodiment of a multi-piece sleeve. The sleeve 21 comprises a first opening 25 at the proximal portion of the sleeve, a second opening 27, with a beveled tip, at the distal portion of the sleeve and a tapered portion 29 with the connection 31 between the two pieces preferably positioned just distal to the tapered portion 29. The sleeve pieces can be used as an intact sleeve or the portion of the sleeve including the first opening 25 can be discarded while that portion of the sleeve including the second opening 27 and the lens 50 can be used separately. Alternatively, a lens in a uniformly tubular sleeve can also be employed, such as that portion of the sleeve with opening 27 as illustrated in FIG. 5b. The multi-piece lens can be used, for example, with the front loading device of FIG. 9, as described below.

In one embodiment, both proximal and distal portions of the sleeve are prepared from ETFE, PTFE, or the like, and in another embodiment that part of the sleeve including second opening 27 is prepared from ETFE or PTFE while that portion of the sleeve including first opening 25 can comprise an elastic portion such as a soft silicone, an elastomeric latex, or another flexible material. Alternatively, the multi-piece sleeve can be prepared from materials with different hardnesses. In one example, that portion of the sleeve including first opening 25 can be prepared from a flexible, deformable material while that part of the sleeve including second opening 27 can be more rigid. Where the sleeve 21 is provided as a multi-piece sleeve, preferably the portions of the sleeve are affixed to each other by any suitable method or material including, but not limited to, an epoxy bond, a heat bond, silicone adhesive, acrylic adhesive, welding (e.g., ultrasonic, laser, etc.).

The sleeves of this invention are compressible, deformable and preferably flexible and malleable. The sleeves protect the implant from damage and provide a cost effective delivery system for introducing an implant into the body. Preferred dimensions of the sleeve at the narrower end (the second opening or tubular portion of the sleeve) is preferably 1.5 mm to about 4.0 mm in diameter and the preferred length of the sleeve is from about 10 mm to about 50 mm depending on the particular application of the insertor apparatus. The thickness of the wall of the first opening is preferably about 0.01 mm to about 0.1 mm. The thickness of the wall of the second opening is preferably about 0.15 mm to about 0.35 mm. Preferably the tubular portion of the wall is constant from the second opening to the distal end of the tapered portion. This disclosure includes a number of variations that all employ the sleeves of this invention. Those of ordinary skill in the art will recognize that the sleeves of this invention can further be incorporated into a variety of implantation devices including, but not limited to, intraocular lens inserters and injectors.

The hand-piece, pusher element, collet and ring clamp can be prepared from a variety of durable, stiff materials such as hard plastics, including moldable plastics, acrylics, styrene, clear, opaque or non-opaque materials. Those with ordinary skill in the art will appreciate the advantages of a non-opaque collet, for example, that permits the continued viewing of the lens during insertion. Hand-piece 12 and other hand-pieces of this invention can further be prepared from stainless steel, polysulfone, polycarbonates, nylons, acetals or other suitable materials with or without glass, carbon or graphite fillers. The pieces can be prepared from heat or irradiation-stable materials for reuse or prepared as a disposable for single-use applications.

The sleeves of this invention are preferably disposable, and as discussed further below, the sleeves can be supplied with or without an implant. Where the sleeves of this invention are reused, care is taken to monitor wear of the sleeve and preferably, the sleeves are treated for microbial contamination before reuse.

Referring again to FIG. 1, the device 10 includes a collet 18 to engage sleeve 20 and maintain orientation of sleeve 20 in the device. Collet 18 is substantially hollow to form an internal lumen 47 (FIG. 1b) and comprises a proximal end 42 and a distal portion 46. Collet 18 is preferably slightly tapered down its length and in a preferred embodiment, collet 18 includes at least two slits 43 (see FIG. 1a) for immobilizing the sleeve in the device and a notched portion 49, or other means, for engaging hand-piece 12 and preventing rotation of hand-piece 12 relative to collet 18 during use. Those of ordinary skill in the art will recognize that there are a variety of modifications to the collet, hand-piece or ring-clamp that could be used to immobilize the sleeve of this invention and that, for purposes of this invention, an immobilized sleeve is an important and preferred aspect of this invention.

In a preferred embodiment, the internal lumen 47 of the collet 18 tapers toward the distal portion 46 of collet 18 to guide blades 16 toward the implant and to permit the blades to track smoothly as they advance the implant toward second opening 26 of sleeve 20. FIG. 4 provides a number of cross-sectional views looking down the length of collet 18 from the distal portion 46 and including lumen 47. The distal portion 46 of collet 18 can take on any of a variety of cross-sectional configurations as illustrated in FIG. 4. FIG. 4a illustrates a round configuration; FIG. 4b a rhomboid configuration; FIG. 4c a winged circular configuration; FIG. 4d an expanded winged circular configuration; FIG. 4e an even more expanded winged circular configuration; and FIG. 4f a scrolled configuration. Two edges of the rhombus (FIG. 4b) and the winged portions by cross-section (FIGS. 4c–4f) are available as guides for blades 16.

In addition to the modifications to the distal portion of the internal surface of collet 18 (FIG. 4), the internal surfaces of the lumen formed in collet 18 can be modified in other ways. For example, lumen 47 can be modified as illustrated in cross-section G—G through collet 18 (see FIG. 1b). This shape provides guidance and lateral stability to blades 16. Alternatively, modifications to the internal surfaces of the collet or where a collet is not used, the internal surface of the hand-piece can include guides such as those provided in FIG. 11 or follow those of Rheinish et al. (U.S. Pat. No. 5,275,604). Further, the cross-sectional dimension of the internal lumen of the collet also preferably narrows from the proximal portion toward the distal portion of the collet 18 to permit blades 16 to track smoothly into contact with sleeve 20 when sleeve 20 is loaded into device 10. Importantly, the guides are positioned outside of the flexible sleeve and therefore do not contact the implant directly.

Hand-piece 12 (FIG. 1) includes an elongate shaft preferably with a flange 45 at its proximal portion and threads 55 at its distal portion. Hand-piece 12 is preferably substantially hollow and is adapted to receive pusher 14. Distal portion 48 (see FIG. 7) of hand-piece 12 is preferably adapted to receive notched portion 49 of collet 18. Distal portion 48 is also preferably threaded to receive ring clamp 22. Optionally, hand-piece 12 also includes grips such as longitudinal grooves or roughened portions along its length to prevent sliding and unwanted rotational movement during use.

Pusher element 14 is preferably an extended rod that is adapted to fit within the hollow portion of hand-piece 12 and to mate in contour with hand-piece 12. Pusher element 14 preferably includes a broadened proximal portion 51 to facilitate movement of the pusher element 14 relative to hand-piece 12. Optionally, guides or ridges on the outer surface of pusher element 14 can be added to mate with matching receiving guides within the hollowed portion of hand-piece 12.

Preferably the device 10 is equipped with at least two blades 16 affixed to the distal portion of pusher element 14. The blades 16 can be prepared from a variety of materials including, but not limited to, TEFLON, plastic, metal-reinforced plastic, stainless steel or other rigid materials. In a preferred embodiment, blades 16 are prepared from stainless steel wire, such as hard spring temper type 302 stainless steel wire rolled flat having a tensile strength of about 280,000 psi or type 17-7 precipitation hardening (PH) stainless steel drawn wire rolled flat and then heat treated to 240,000 psi in a vacuum or as much as 320,000 psi (Supreme Steel Treating Inc., El Monte, Calif.). However, steel wire greater than about 60,000 psi is also considered suitable for the blades of this invention. Those of ordinary skill in the art will recognize that the rigidity of the blade is a function of the type of material, the length of the blade and the thickness of the blade and that the selection of the material will also take into account the type of implant to be inserted into a portion of the body. Some plastics can be used, but plastic blades may be thicker than steel blades to provide sufficient rigidity to the blades.

In a preferred embodiment, using two blades for lens insertion, the blades 16 are at least 1 centimeter (cm) in length and preferably less than about 10 cm in length. For an intraocular lens embodiment, the blades are preferably greater than about 3.5 cm and preferably less than about 6 cm in length and more preferably less than about 4.5 cm in length. Also preferably, each blade is preferably at least about 1 mm in width and preferably less than about 10 mm in width. The length that the sleeve is selected to extend beyond collet 18 can vary and the length of blades 16 will vary with this length. Also preferably, each blade is at least about 0.25 mm in thickness and preferably less than about 1.5 mm in thickness. However, blades of as thin as 0.1 mm could function in a small, compact insertor.

In a preferred embodiment, the blades 16 are formed such that the tips of the blades bend slightly together. Those skilled in the art will recognize that the extent of the bend in the blades can be varied somewhat, particularly depending on the overall dimensions of the device. For example, the blades can be bent or curved in a slight arch or curved or bent slightly inward toward each other at one or more locations along the length of the blades. For example, blades can be curved inwardly from about 1 mm to about 10 mm relative to the plane formed by the blade. Alternatively, the tip of the blade can be bent slightly such as from about 0.02 mm to about 0.2 mm relative to the plane formed by the blade. Blades 16 can be polished, as needed, to further reduce friction of the blades either in the hand-piece 12, the collet 18, or on sleeve 20. The blades can be affixed to the pusher element using adhesives, crimping, pinning or a variety of means known to those of ordinary skill in the art.

While the invention has been disclosed by way of the use of two blades, those of ordinary skill in the art will appreciate that a number of blades can be used. For example, it is possible to employ a single immobilized blade, prepared as a blade or as a portion of the collet, together with a single movable blade to apply an off-set force that squeezes the sleeve at a point proximal to the implant to advance the implant toward the distal portion of the sleeve. Alternatively, the device could employ three, four, or more blades positioned concentrically around the sleeve. Also alternatively, a single flat blade could move or alternatively be immobilized and two smaller blades could assist in advancing the implant through the device using the pusher 14. Further, rather than a blade, a solid ring or cylinder fitted over the sleeve can be used in place of one or more blades to advance an implant down a sleeve. The blades can also be fitted with guide grooves or ridges to assist in the axial tracking of the blades through the device.

In a preferred embodiment, illustrated in FIG. 1, the blades are substantially flat, however; those of ordinary skill in the art will also appreciate that the blades can be wider and flattened to a greater degree than the blades illustrated in FIG. 1. Alternatively, the blades can be cylindrical in shape, curved or ovoid. Again, the shape, width and thickness of the blade can be selected based on the type of implant, the dimensions of the implant, as well as the choice of blade material. Preferably, care is taken so that the edges of the blades are smooth and do not tear or substantially deform the sleeve during use.

Alternatively, the blades 16 can be configured similar to the blades of a tweezer. In yet another embodiment of this invention, blades 16 can also be encased in a layer of protective material, such as a layer of tubing, or an external, preferably transparent sheath, such as a separate flexible sheath or multiple lumen tubing, or a sleeve where at least the inner lumen containing the implant is compressible and flexible and where the blades are encased each in their own covering within a second lumen that encompasses both the sleeve and the blades. Alternatively, the second lumen can be prepared from a rigid material to enclose the blades as they advance the implant, for example, such as where the blades do not extend beyond the distal portion of the hand piece.

The squeezing action of a blade or blades on a flexible and compressible sleeve containing one or more implants produces a controlled and deliberate movement of the implant through the sleeve along a predetermined axis of motion, defined by the sleeve, and at a controlled rate. The blades provide a means for compressing a sleeve and a means for advancing the compressed area of the sleeve toward the distal end of the sleeve. Those of ordinary skill in the art will recognize that other mechanisms employing these means can be incorporated into the devices of this invention. Those of ordinary skill in the art will recognize that forces on the flexible and compressible sleeve from the blade(s) and the frictional forces between the sleeve and the implant can be increased or decreased to maximize controlled movement of the implant through the device and into the body.

Device 10 also includes a ring clamp 22 adapted to fit over collet 18 and to secure onto hand-piece 12. Ring clamp 22 further compresses the sides of collet 18 to squeeze clamp the sleeve 20 within the collet 18 during use. Those of ordinary skill in the art will recognize that the ring clamp is not necessary and that device can be configured to secure the collet or its equivalent to the pusher element and to immobilize the sleeve in a variety of ways. Alternatively, the collet can be included as part of the hand-piece, such as for example, in the front-loading device discussed below.

Optionally a stopping mechanism, such as a stop bar or a key is positioned along the length of the hand-piece to mate with an extension on the pusher. A stop bar or key can be used to stop the blades and the pusher element from pulling out of the hand-piece or extending further than desired from the distal end of the collet. A key 214 is used in FIG. 11.

To assemble device 10, a sleeve 20, preferably containing a lens 50 (see FIG. 1) between second opening 26 and tapered portion 28 (i.e., preferably substantially within the tubular portion of the sleeve) is introduced into lumen 47 of collet 18. Referring again to FIG. 1, illustrating a preferred view of the proximal portion of collet 18 by cross-section. That portion of the sleeve 20 with second opening 26 is introduced into the length of collet 18 such that first opening 24 of sleeve 20 is positioned within the proximal portion of collet 18 and is positioned between slits 43 but preferably does not extend beyond slits 43 past the dimension of collet 18. Second opening 26 of sleeve 20 preferably extends beyond the distal portion of collet 18. Pusher element 14 with blades 16 is then introduced into hand-piece 12. Next, blades 16 are positioned on either side of sleeve 20 and moved toward the distal portion of the collet 18 preferably until resistance is felt on the blades due to the contact between blades 16 and that portion of sleeve 20 containing lens 50. Collet 18 is next positioned onto the distal portion of hand-piece 12, preferably mating notch 49 on collet 18 with a groove on hand-piece 12. Ring clamp 22 is positioned over sleeve 20 and around collet 18 and is securely engaged onto the distal portion of hand-piece 12. In use, pusher element 14 is pushed forward to move blades 16 down the length of sleeve 20 to gently urge lens 50 out of sleeve 20.

FIG. 6 provides a cross-sectional view of the assembled device 10 in cross-section and FIG. 7 provides a second cross-sectional view of the assembled device rotated 90° relative to FIG. 6. Here, sleeve 20 contains a lens 50. The proximal portion containing first opening 24 of sleeve 20 is engaged within the proximal portion of collet 18 and collet 18 is positioned onto the distal end of hand-piece 12. Pusher element 14 is positioned within hand-piece 12, blades 16 are positioned on either side of sleeve 20 and ring clamp 22 is in place to secure sleeve 20 within collet 18 and to further secure collet 18 onto hand-piece 12. Movement of pusher element 14 relative to hand-piece 12 moves blades 16 toward the distal portion of the device and gently squeezes or urges lens 50 forward and out of sleeve 20.

Figure 8:
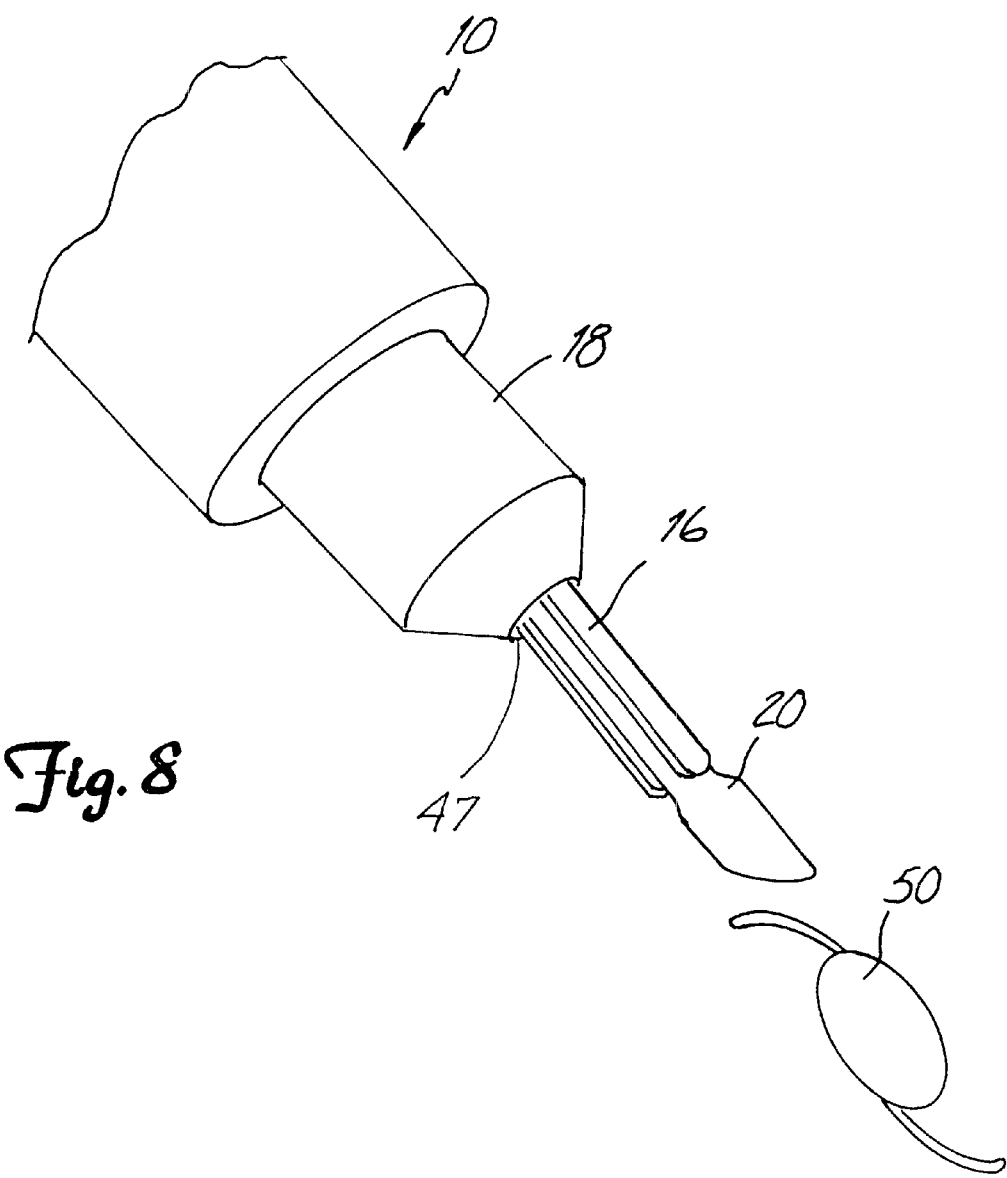
FIG. 8 is a perspective view of the distal portion of an assembled insertor device according to this invention.

FIG. 8 is a perspective view of the distal portion of an assembled device 10. Here collet 18 is depicted with blades 16 extending from lumen 47 of collet 18 with lens 50 having been squeezed or urged from sleeve 20 by movement of pusher element 14 and blades 16 distally down the length of sleeve 20.

Figure 9:
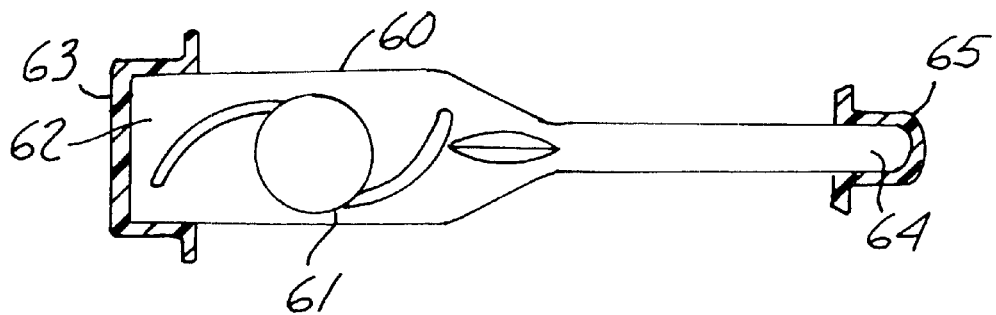
FIG. 9 is a cross-sectional view of a lens preassembled in a sleeve.

In use, the physician can purchase the sleeve either alone or preassembled with an implant, such as a lens already positioned within the sleeve. FIG. 9 illustrates a sleeve 60 with a lens 61, here an intraocular lens, positioned near first opening 62 at the proximal end of sleeve 60. A cap 63 or other sealing means, such as heat bonding, an adhesive, or the like is used to seal the proximal portion of sleeve 60 (that portion including first opening 62). In FIG. 9, the second opening 64 is also capped with a second cap 65 or otherwise sealed, such as by heat bonding, an adhesive, or the like. The sleeve alone or the sleeve with the lens is provided in sterile form to the physician and where the implant is shipped in the sleeve, the sleeve preferably is filled, at least in part, with a suitable friction reducing material such as a lubricant or buffer, including a viscoelastic (i.e., an aqueous suspension of water and up to 10% of a composition including, for example, sodium hyaluronic acid, (i.e., HEALON), chondroitin sulfate, a cellulose such as HPMC (hydroxypropylmethyl cellulose), or a combination thereof) or a biocompatible liquid such as a variety of buffers known in the art, including phosphate buffers, saline, and the like.

Where the sleeve is supplied alone without an implant, the surgeon can optionally remove the caps or otherwise open the sleeve and introduce a suitable lubricant, by syringe or pipette, into one or both ends of sleeve 60 before introducing the implant into the sleeve. Where a syringe or pipette is used, care is preferably taken to maintain the integrity of the sleeve while the lubricant, buffer, or the like is added. Next, the implant, such as a lens, and preferably an intraocular lens, is placed inside the first opening. If a forceps is used, care is taken to gently position the lens just inside the first opening or alternatively positioned directly into the tapered portion and into at least part of the tubular portion of the sleeve. Optionally, the implant can be deformed, such as by using a forceps, prior or concurrently with the introduction of the implant into the sleeve. Where the implant is a lens, the implant can be folded slightly (i.e., less than 20% of the diameter of the lens) or substantially (i.e., greater than 50% of the diameter of the lens) before the lens is introduced into the sleeve. Preferably, where the implant is a multi-piece intraocular lens with filament haptics, the lens is introduced into the sleeve with one haptic positioned in front of the lens and the second haptic trailing the lens. However, those skilled in the art will recognize that the lenses can be put into a sleeve in a variety of orientations without altering the scope of this invention. This invention is designed to accommodate a variety of implants, including a variety of lenses and a variety of intraocular lenses including, but not limited to, single piece intraocular lenses and three or more piece composite intraocular lenses that employ a plurality of haptic supports.

Referring again to FIG. 2, preferably, once a lens 50 is positioned within the sleeve 20, a separate squeezing tool, such as tool 52 can be used to gently position the lens, at least in part, in the tapered portion 28 and preferably at least in part, past tapered portion 28 and into the distal portion or tubular portion of sleeve 20, such as illustrated in FIG. 1. Squeezing tool 52 includes an elongate channel 54 into which first opening 24 of sleeve 20 is introduced. Once in place, tool 52 is advanced toward the distal portion of sleeve 20 with sleeve 20 passing in part, through channel 54 for a distance sufficient to urge lens 50 into position in sleeve 20 preferably past tapered portion 28. Sleeve 20 can then be assembled onto one of the devices of this invention. An alternative to the squeezing tool 52 is the use of the fingers to gently urge or otherwise nutate the implant through a sleeve.

The channel 54 of squeezing tool 52 can take on a variety of shapes. Preferably channel 54 is sufficiently long to accommodate the first opening 24 of sleeve 20. In a preferred embodiment, the channel is an elongate slit extending through squeezing tool 52 and preferably the channel is curved slightly. The channel 54 can be uniform in its height or the channel can vary in height or shape of the channel to facilitate varying dimensions of the implant. In a preferred embodiment, the channel 54 of squeezing tool 52 is shaped in an upward-curving or upward-angled manner, as illustrated in FIG. 2, relative to the orientation of sleeve 20 when it is inserted in the squeezing tool 52 to promote the folding up of the lens in the sleeve such that when the lens is introduced into the eye, the edges of the lens open downward in the eye, much like a flower unfolding, to minimize trauma to the eye as the lens opens from its folded position. The folding of the lens is further assisted by the cross-sectional configuration of the sleeve, such as by a pleat or a "V" shaped cross-section. The actual squeezing tool can take on a variety of geometries, for example in FIG. 2 is rectangular in shape. Circular, square, or ovoid shaped squeezing tools could also be used and one of ordinary skill in the art can imagine a variety of shapes to the tool to facilitate its stabilization in the hand and to ease use. The squeezing tool 52 or gentle urging with fingers overcomes the damage to lenses that can be seen in devices that use a push-rod to directly contact the lens and advance the lens through these devices.

Figure 16A:
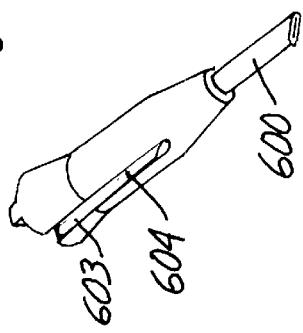
FIG. 16a is a perspective view of a sleeve with an intraocular lens for insertion into a collet.
Figure 16B:
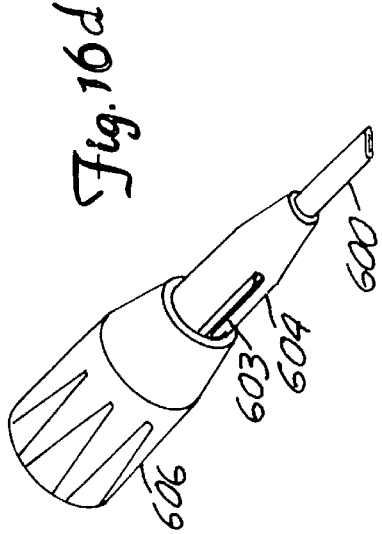
FIG. 16b is a view of an assembled sleeve and collet.
Figure 16C:
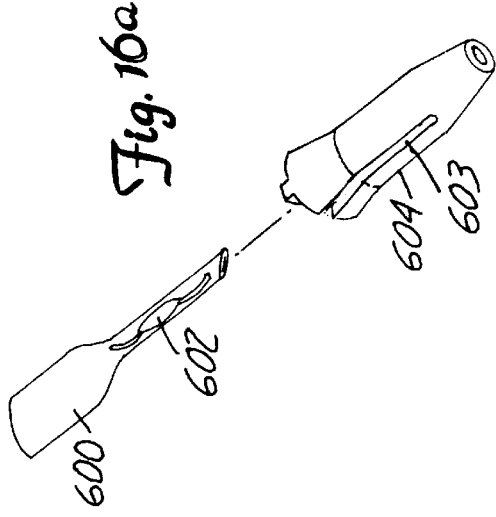
FIG. 16c illustrates assembly of a ring clamp onto the collet and FIG. 16d illustrates an assembled sleeve in a collet positioned with a ring clamp.
Figure 16D:
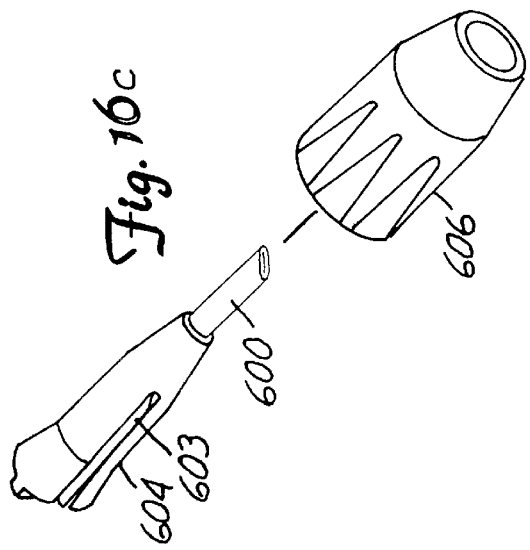

In a preferred embodiment, as illustrated in FIG. 1, the implant is positioned in the sleeve and the sleeve is positioned through collet 18. Collet 18 is then positioned onto pusher element 14 and ring clamp 22 is used to immobilize the sleeve 20 on hand-piece 12. FIG. 16 illustrates the assembly of a sleeve 600 with an intraocular lens 602 into a collet 604. In FIG. 16*a* *the sleeve is preferably positioned in the collet 604 with the second opening of the sleeve extending from the distal portion of the collet (see FIG. 16b).* The edges of the sleeve proximal to the first opening of the sleeve preferably extend at least to the edge of the slits 603 on either side of the collet. Once the sleeve 600 is assembled in the collet 604, a ring clamp 606 is positioned over the collet (see FIG. 16c). Next, the ring clamp is secured to the hand piece thereby securing the collet to the hand-piece and exerting pressure on the collet to compress the slits 603 to immobilize the sleeve 600 on the device (see FIG. 16d). As illustrated in FIG. 17a, a cross-section of the device through D—D of FIG. 17b, while assembling the ring clamp onto the hand-piece 608, blades 610 and 612 are positioned on either side of the sleeve within the lumen of the collet as illustrated in FIG. 17c. The assembled device of FIG. 17 is provided in FIG. 17b.

Following appropriate incisions, the device is positioned in the eye, preferably such that a beveled portion of second opening 26 of sleeve 20 (FIG. 2) is positioned downward. The pusher element 14 is advanced slowly toward the distal portion of the device and the lens, positioned in the sleeve such that the lens is folded upwards, is released into the eye with the folded edges opening downward, toward the eye as the lens is allowed to unfold.

Advantageously, the lens is oriented and folded consistently in sleeve 20 through the use of one or a combination of the squeezing tool 52, the cross-sectional configuration of at least the tapered portion 28 of sleeve 20, as illustrated in FIG. 3, a forceps and/or through the use of folding guides positioned on the internal surface of the lumen of collet 18. Alternatively, the lens can be loaded and advanced past the tapered portion of the sleeve, in whole or in part through the use of forceps or other devices. A sleeve stabilizing device is provided in FIG. 19 to assist in loading an implant. This device is discussed infra.

There are other configurations for insertor devices within the scope of this invention. In another example, the device is a front loading insertor device. Referring now to FIG. 10a, which illustrates in cross-section a preferred embodiment of a front-loading device for insertion of an implant in the body. The device 100 includes a hand-piece 112 and a pusher element 114. The hand-piece 112 preferably includes an elongate body and a tapered portion 120 with distal opening 121.

The pusher element 114 includes a sleeve holder 115. Sleeve holder 115 could take a variety of forms such as a post, one or more blunt barbs, one or more grooves, or the like. Pusher element 114 further includes blades 122 mounted on distal block 124 in pusher element 114. Blades 122 pass on each side of sleeve holder 115. The device further includes a sleeve 116 affixed to sleeve holder 115. Sleeve 116 extends in a reverse orientation as compared to the sleeve orientation of FIG. 1. In FIG. 10a, sleeve 116 is illustrated with a substantially tubular portion 117, a tapered portion 119, preferably at least one pleat 113 and a first opening 118.

In this embodiment a lens or other implant is loaded into the sleeve using the methods disclosed in association with FIG. 2 except that what is the second opening in FIG. 2 is now affixed to sleeve holder 115 in FIG. 10a. A forceps can be initially used to position an implant in first opening 118 or to position the lens completely in the tubular portion of the sleeve, A squeezing tool 52 or a forceps can then be used to urge the implant just past the tapered portion 119 of the sleeve or at least toward what was the second opening of the sleeve of FIG. 2 and is now that portion of the sleeve affixed to sleeve holder 115 (FIG. 10b).

Once the lens is loaded, that part of sleeve 116 including the first opening 118 and the tapered portion 119 are separated from the portion of the sleeve including the lens. In some embodiments, the sleeve 116 can be cut either with a sharp blade or scissors. Alternatively, a guillotine-type device can be used to sever the sleeve as a blunt-cut, a beveled cut, and the like.

Pusher element 114 is advanced toward tapered portion 120 of hand-piece 112. With this movement, blades 122 advance or mobilize the lens, again by squeezing or urging, into the tapered portion 120 of hand-piece 112, as illustrated in FIG. 10b.

In yet another embodiment of this invention, the device is supplied pre-assembled with a sleeve having a lens positioned therein. Preferably the lens is supplied in a substantially unfolded state, but those of ordinary skill in the art will understand that with the development of new or different lens materials or configurations it may be possible to supply the device with a sleeve and a lens, or other implant, deformed within the narrow portion of the sleeve, ready for insertion.

In an embodiment, illustrated in FIG. 11, a device 200, having a hand-piece 205 can be prepared in one piece or in two pieces. A single-piece hand-piece is illustrated in FIG. 11a. Here, the device includes a hand-piece 205 and a pusher element 204. The hand-piece 205 preferably includes an elongate body with a proximal flange 203, a tapered portion 206 and a lumen 202. The hand-piece 205 includes a distal opening 208. The pusher element 204 includes a sleeve holder 210. Sleeve holder 210 can take a variety of forms, as described above. Pusher element 204 further includes blades 212 mounted on a proximal block 214 of pusher element 204. Blades 212 pass on each side of sleeve holder 210.

A removable key 214 is positioned on pusher element 204. Sleeve 216 is preferably provided with a lens 218 positioned therein. A first end of sleeve 216 is affixed to sleeve holder 210 and a second opening 222 of sleeve 216 is preferably sealed, such as with a cap 224 or seal.

In use, pusher element 204 is advanced toward tapered portion 206 of hand-piece 205. With this movement, blades 212 advance the lens into the tapered portion 206 of hand-piece 205, as illustrated in FIG. 11b.

The pushing mechanism of FIG. 11 is a multi-step mechanism, here a two-step pushing mechanism. A key 214 is removed from the pusher element 204 after pusher element 204 has been partially advanced. Now pusher element 204 can completely advance toward the distal portion of the device, blades 212 are free to advance the lens with pusher element 204 and the lens is moved through sleeve 216, out of device 200 and into the eye, as illustrated in FIG. 11c. Multi-step pushing mechanisms are useful for increasing control over the release of the lens from insertor devices.

In another embodiment of the inserters of this invention, the hand-piece is prepared in multiple pieces, preferably in two pieces. This is particularly useful where the insertor is provided preassembled with a lens positioned in a sleeve. An example of this embodiment is provided in FIG. 12a. Here the device 250 includes a hand-piece 252 that further includes a distal portion 254 at the distal aspect of the hand-piece and a proximal hand-piece portion 256. The distal portion 254 includes a tapered nose 258 including a distal opening 260. A septum 262 preferably traverses the lumen of hand-piece 252 and includes a sleeve holder 264. Sleeve holder 264 is available to secure a sleeve 266 onto the device 250. A pusher element 268 includes an elongate shaft to mate with the lumen of hand-piece 252 and at least one blade, and preferably two blades 270 are preferably affixed thereto. The internal surfaces of the distal portion 254 of hand-piece 252 can include external folding guides 272. One example of these guides is provided in the cross section shown in FIG. 12b. The folding guides are termed external folding guides to differentiate these guides from the cross-sectional configuration of the sleeve that provides internal folding guides for the lens (such as the pleats and the cross-sectional configurations of FIG. 3). The external folding guides 272 can take a variety of configurations and in a preferred embodiment, the cross section of distal portion 254 is substantially rhomboid in cross-section with preferably two grooves to urge the lens into a folded conformation. Other cross-sections to distal portion 254 are possible as are other folding guides. Other folding guides are discussed in U.S. Pat. No. 5,275,604 to Rheinish et al.

Referring again to FIG. 12a, a lens 274 is preferably supplied in sterile form in a capped 276 or otherwise sealed sleeve 266. Optionally the sleeve can be supplied preloaded with a buffer compatible with the eye, or with a solution compatible with another portion of the body receiving the implant. During assembly, the lens 274 is positioned in the sleeve 266 and sleeve 266 is affixed to device 250 via sleeve holder 264. Hand-piece 252 portions 254 and 256 are assembled on the devices to surround the sleeve 266 and lens 274. Hand-piece 252 portions 254 and 256 can be joined by a variety of means including, but not limited to, screw-type threads, grooves, notches, clamping mechanisms, snapping mechanisms, adhesives, and the like. Preferably, once assembled, the hand-piece 252 is not readily separable nor is the hand-piece preferably separable from the pusher element 268.

In use, cap 276 is removed from sleeve 266. Pusher element 268 is advanced toward distal portion 254 of hand-piece 252 to advance blades 270 behind lens 274 and advance lens 274 from the sleeve through opening 260 and into the eye. Preferably, after use, device 250 is disposed. It is noted that the insertor of FIG. 12 can also incorporate the two-part pushing element design of FIG. 11.

Sleeve 266 is preferably provided preassembled on the device with the lens in place and affixed to sleeve holder 264. Sleeve 266 preferably includes a suitable lubricant, a friction reducing material, implant stabilizer or buffer. Where a lubricant or buffer is not included with the implant, the sleeve can be filled with a suitable lubricant or buffer before use.

In another variation of this invention, the pusher element can be advanced using a threaded mechanism, such as screws, rack and pinion, or any other mechanism. These mechanisms can provide added control when the lens is being advanced by the blades.

In another preferred device 300 according to this invention (see FIG. 13), a hand-piece 312 preferably includes an elongate body having a proximal end 314 and a distal end 316. The distal end 316 preferably includes a tapered portion 318 and a canal 320 communicating with a lumen 322. The canal 320 also communicates with a slot 324 that is positioned proximal to canal 320 on hand-piece 312. A hole 326 is positioned from slot 324 to an external aspect of hand-piece 312 and is adapted to receive a sleeve clamping thumbscrew 327. Sleeve 328 is a flexible, compressible sleeve with a first opening 330, a second opening 332 and a tapered portion 334 positioned therebetween. In a preferred embodiment, the second opening is preferably beveled. An implant, such as a lens 342, is introduced into sleeve 328 and advanced toward the distal portion of the sleeve either using the squeezing tool 52, as illustrated in FIG. 2, or by gently urging the implant into the sleeve, past the tapered portion using a forceps, or the like.

Once sleeve 328 is loaded with an implant, the sleeve is positioned in handpiece 312. The second opening 332 of sleeve 328 is passed through lumen 322 and the first opening 330 of the sleeve 328 is positioned into slot 324. Sleeve clamping thumbscrew 327 is tightened to immobilize sleeve 328. In one aspect of this embodiment, a squeezing blade assembly 336 including at least one blade, and preferably two blades 338 are connected to a thumb-engaging portion 340. The squeezing blade assembly 336 is positioned on either side of sleeve 328 and before thumb-engaging portion 340 is mobilized, blades 338 are positioned just proximal to lens 342. Movement of the thumb-engaging portion 340 along the axis of hand-piece 312 toward the distal end 316 of device 300 results in the egress of lens 342 from sleeve 328. In an alternative embodiment of the device of FIG. 13, the thumb screw 327 is replaced with a ring clamp to immobilize the sleeve 328. Thumb knobs can be added to the squeezing blade assembly as desired.

In yet another embodiment, the sleeve can be used separately as an insertor without using the hand-piece portion of this invention. For example, a sleeve, such as illustrated in FIG. 2 is loaded with an implant, such as a lens, as provided above. The sleeve itself can be used to directly deliver the lens by clamping a portion of first opening 24 of the sleeve with a forceps or suitable hemostat-type device. In this embodiment a push-rod, such as a small cylindrical bar, can be introduced into the sleeve after the implant has been inserted and positioned in the sleeve by squeezing or urging the implant towards the distal end. The implant is mobilized using direct force applied to the implant by the push-rod to introduce the implant into the body. Alternatively, a squeezing tool, such as that illustrated in FIG. 2, or a modification of the squeezing tool (for example, with an added handle, or the like) can be used to position the lens in the sleeve or a squeezing tool can be use to advance the implant into the tapered portion of the sleeve, toward the second opening of the sleeve and past the second opening and into the body. In a further embodiment, the implant is advanced through the sleeve using fingers to gently urge the lens by nutating and/or gently pinching the sleeve behind the implant. In yet a further embodiment, the sleeve can be rolled from the first opening 24 to the second opening to advance the lens or another implant through a sleeve. In some of these embodiments, a squeezing motion is used to advance the lens, at least in part, through the sleeve. The ability of the sleeve to be squeezed through a squeezing device, manipulated by fingers to advance an implant or to roll up a portion of the sleeve to advance the implant also speaks to the nature of the sleeve material. The flexible, compressible, malleable sleeve is prepared from a material that permits ready manipulation of the sleeve as described herein.

Figure 14B:
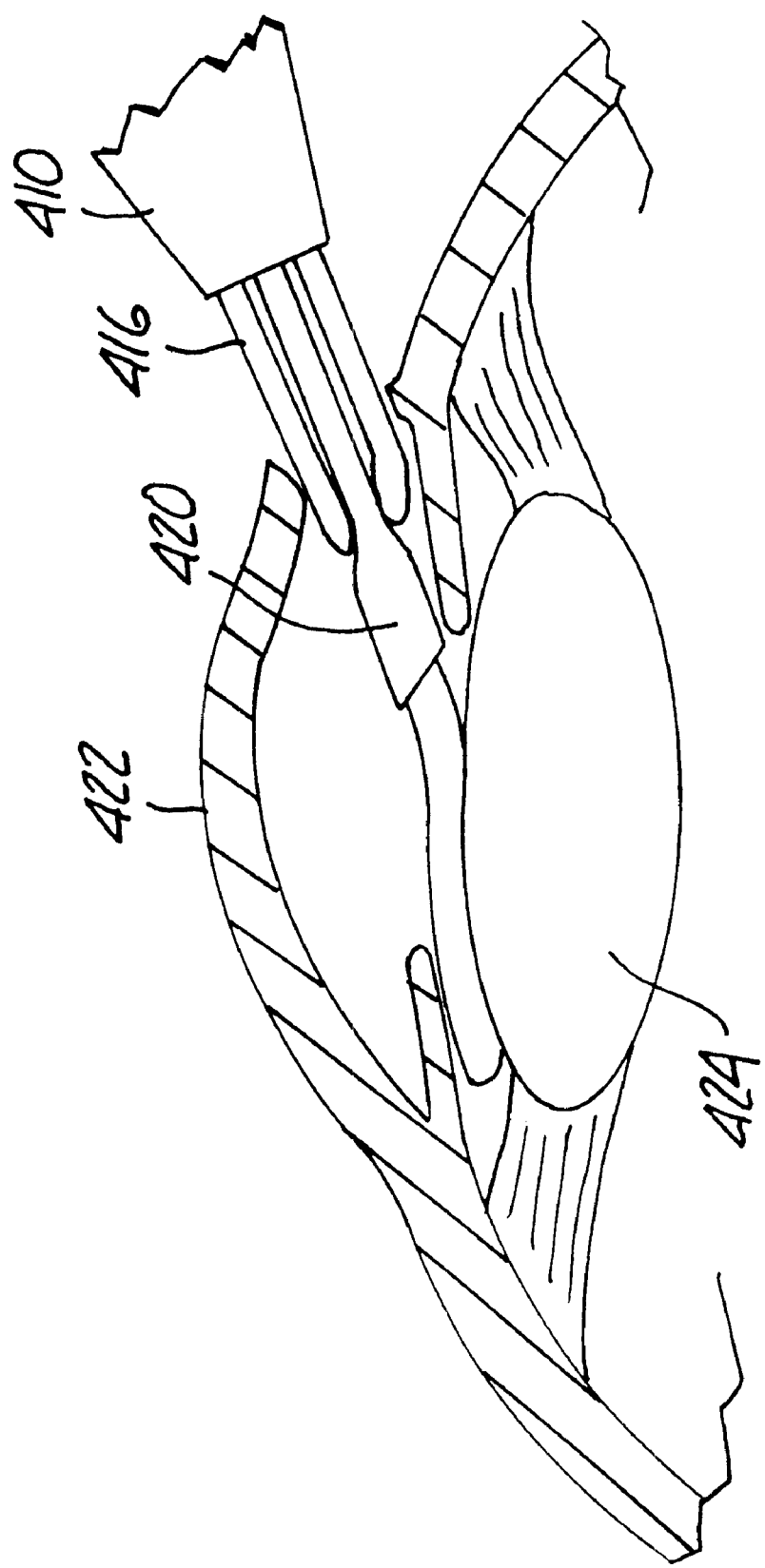
FIG. 14b is a cross-sectional view of an eye receiving an implantable contact lens using a device of this invention.

As noted above, the devices of this invention can position implants in the eye or elsewhere in the body. For example, in a preferred embodiment, illustrated in FIG. 14a, the implant is a lens 450. The lens is advanced using blades 416 on sleeve 420 to squeeze a lens 450 into the eye, generally illustrated as 452. FIG. 14b is a cross section of the eye with a cornea 422, a natural lens 424 and the distal portion 410 of a device according to this invention including blades 416 and a sleeve 420 to advance a lens into the eye. The lens is not necessarily an intraocular lens, but the lens can take the form of an implantable contact lens (ICL) shown in FIG. 14b positioned just anterior to the natural lens 424. Alternatively, the devices of this invention can be used to implant a flexible contact lens onto the surface of the cornea, the device can be used to introduce devices to treat glaucoma or to implant a variety of flexible, solid implants elsewhere in the body.

Figure 15:
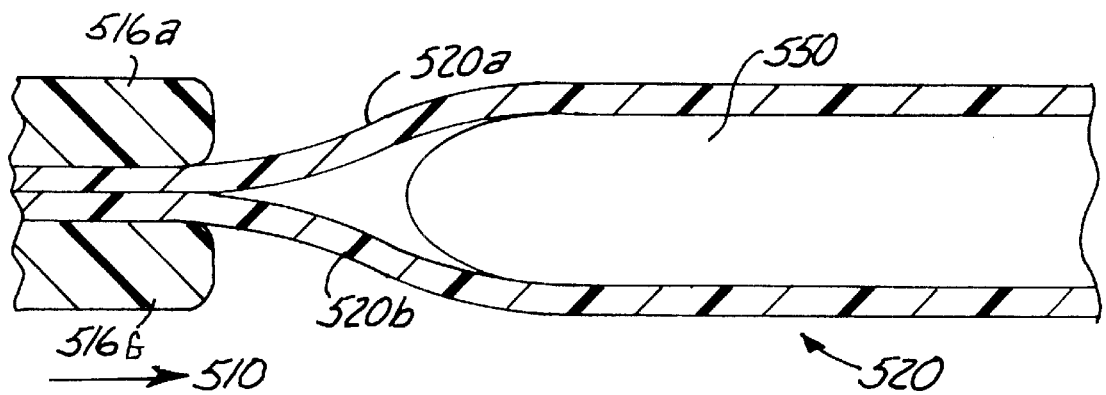
FIG. 15 is an enlarged partial cross-sectional view of the interface between a preferred means for compressing a sleeve in accordance with the present invention.

In several embodiments of this invention, the invention provides a means for compressing a sleeve to advance an implant from the sleeve into a portion of a body. FIG. 15 is an enlarged partial cross-sectional view of the interface between one means for compressing a sleeve in accordance with the present invention. The sleeve 520 includes two side walls 520a and 520b. At least a portion of the side walls 520a and 520b is compressed in the preferred embodiment by blades 516a and 516b as depicted in FIG. 15. Those of skill in the art will, however, understand that many other means for compressing sleeve 520 could be substituted for the disclosed blades.

The compressed portion of the sleeve 520 is then advanced in the direction of arrow 510 towards the implant 550 located between side walls 520a and 520b in sleeve 520. As a result, the blades 516 also function as one preferred embodiment of the means for advancing the compressed portion of sleeve 520 towards the distal end of sleeve 520. Those of skill in the art will, however, understand that many other means for advancing the compressed portion of sleeve 520 could be substituted for the disclosed blades. It is the gentle, squeezing action of sleeve 520 on implant 550 that provides the ability of the present invention to gently deliver an implant in contrast to the known methods.

Those of ordinary skill in the art will recognize that this device has been described by way of using a lens. For other implants, the sleeve configuration can be varied somewhat. For example, while the sleeve would preferably still include a first opening and a second opening, the sleeve may not need a tapered portion, particularly where deformation of the implant prior to insertion is not necessary. Moreover, also depending on a particular insertion application, the dimensions of the device and the dimensions of an incision size can change for a particular application. The cross-section of the sleeve can be narrower or wider, the blade length, sleeve length, hand-piece length can be adjust by ordinary skill in the art to accommodate a variety of implants.

Those of skill in the art will realize that although the devices described in this invention are operated using manual force, similar devices can be prepared using pneumatic, servo-mechanisms including electrical and hydraulic forces, extended flexible cable devices, such as via a foot pedal, or the like without detracting from the scope of this invention.

In one embodiment of this invention, the device is supplied in kit form with an insertor, such as insertor 10 (FIG. 1), a sleeve, in one or two pieces, either empty or already containing the implant and optionally a squeezing tool such as squeezing tool 52. The implant can be supplied with the device or purchased separately. Preferably the device is used to implant a foldable lens and preferably the foldable lens is an intraocular lens.

Figure 19:
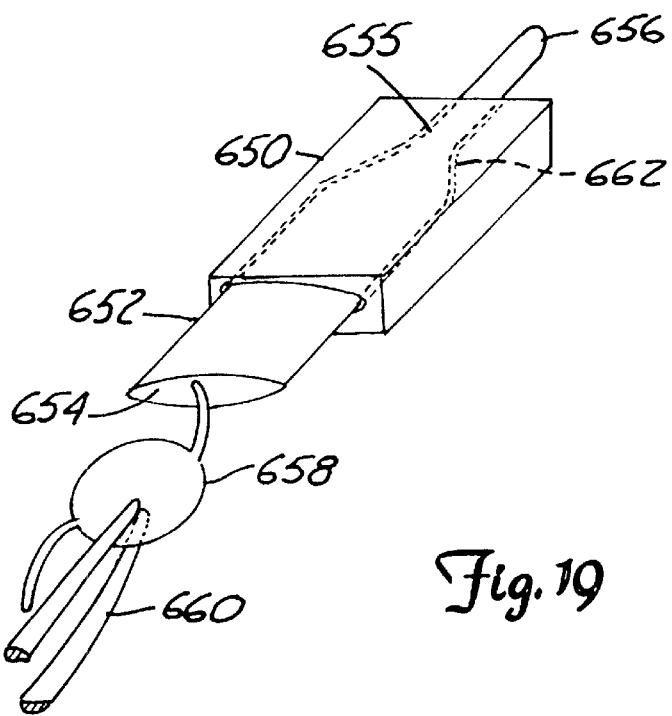
FIG. 19 is a perspective view of a sleeve holder in accordance with another embodiment of this invention.

In another aspect of this invention, the invention includes a sleeve supporting device such as a sleeve holder 650 as illustrated in FIG. 19. The sleeve holder 650 is preferably prepared from a substantially rigid material such as a plastic, including thermoplastic polymers, as well as acrylics, hard silicones, nylon, rubber, and the like. In a preferred embodiment the sleeve holder 650 is prepared from a sufficiently clear material to permit visualization of the implant in the sleeve when the sleeve is in position in the holder. The sleeve holder includes a hollowed portion that is slightly larger but generally and preferably conforms in shape to the shape of sleeve 652 or another sleeve, according to this invention. The sleeve of FIG. 19 includes a first opening 654 and a second opening 656. The first opening 654 is preferably larger than second opening 656 and preferably the diameter of first opening 654 is from about 4.5 mm to about 10 mm and the diameter of the second opening 656 is from about 1.5 mm to about 4 mm. A preferred length of the holder is from about 2 cm to about 4 cm. The sleeve holder adds support to the flexible deformable sleeve during insertion of an implant, such as an intraocular lens 658 into the sleeve. The sleeve holder can take any of a variety of shapes and preferably the shape and size of the holder permit it to be held in one hand while inserting an implant into a sleeve in the holder with the other hand. In FIG. 19, the holder is rectangular in shape, but those of ordinary skill in the art will recognize that a variety of holder shapes and sizes can be prepared to accommodate sleeves in view of this disclosure. Importantly, the pleats 38 in sleeve 20 of FIG. 2 are optional when a sleeve holder such as sleeve holder 650 is used. The combination of a sleeve of this invention with a sleeve holder forms an implant loading system of this invention.

In use, the sleeve is positioned in the block before or after lubricating the sleeve with a suitable friction-reducing agent or buffer. The intraocular lens 658 is inserted into first opening 654 using a forceps 660, fingers, or the like. The lens is urged into the first opening and is positioned preferably past the tapered portion 662 of sleeve 652 and at least partially into the tubular portion 655 of the sleeve. The sleeve is preferably able to distend or stretch to accommodate the additional bulk of the forceps when the forceps is introduced into the sleeve with the implant. Optionally, the implant can be deformed slightly to encourage folding in a desired direction when the implant is introduced into the sleeve, using for example, lateral pressure while introducing the lens into the tapered portion and into 662 at least a part of the tubular portion. The forceps 660 is removed from the first opening 654 and the sleeve 652 is removed from holder 650. The sleeve holder is preferably reusable and can optionally be disposable or sterilizable such as by autoclaving or by exposure to ethylene oxide or ultraviolet light. The other components of this invention (e.g., the hand-pieces, ring clamps, collets, pusher-elements, and the like) can also be sterilized for reuse.

The invention also relates to a kit comprising a sleeve of this invention, an implant, such as an intraocular lens, a corneal implant or another implant according to this invention. Optionally, the kit includes a holder for the sleeve, such as provided in FIG. 19 and optionally the kit includes an insertor device according to this invention. Further the elements of the kit are packing in a tray or package suitable for shipping.

FIG. 18 illustrates an additional insertor device embodiment that employs a flexible, deformable sleeve of this invention together with a push-rod to mobilize an implant from an insertor into a portion of the body. In FIG. 18a, an insertor 700 includes a flexible sleeve 702, a collet 704, and a ring clamp 706. A hand-piece 708 includes a pusher-element 710 or other means for mobilizing a push-rod 712. The push-rod 712 is preferably rounded at the tip 714 to minimize trauma to the implant when the implant is mobilized in the sleeve 702 but the push-rod could also be flattened or grooved. The push-rod 712 is preferably prepared from either the same or similar material as the hand piece or alternatively prepared from stainless steel, TEFLON, acrylic, vinyl, polysulfone, or the like.

To assemble, the sleeve 702, collet 704 and ring clamp 706 can be assembled as described in regard to FIG. 16. The push-rod 712 preferably extends from the hand-piece sufficiently that it can be positioned within the first opening of the sleeve 702 as the ring clamp 706 is position and affixed to the hand-piece 708. At least one indexing extension 713 preferably extends from the distal portion of the hand-piece to key or mate with the proximal portion of the collet (as illustrated in the proximal portion of the collet of FIG. 16). The extensions prevent rotation of the collet relative to the hand-piece as the ring clamp is secured to the hand-piece. The ring clamp 706 secures the collet to the device and provides a clamping force to immobilize sleeve 702 between slits 716 of collet 704.

In another variation, the sleeve with an implant is positioned over the push-rod 712. Where an intraocular lens is used, care is taken to align the push-rod with the body of the lens so that the haptics are free to move within the sleeve. Next, collet 704 is placed over the sleeve and positioned onto hand-piece 708 using extensions 713. The ring clamp 706 is next positioned onto the device.

The assembled device is provided in FIG. 18b and the distal end of collet 704 for the push-rod device is preferably illustrated in FIG. 4a. A cross-section of the device through E—E of FIG. 18b is illustrated in FIG. 18c. Here ring clamp 706 surrounds the proximal portion of collet 704. Sleeve 702 is positioned within the lumen 718 of collet 704 with push-rod 712 positioned within sleeve 702. Ring clamp 706 provides a clamping force to immobilize sleeve 702 within the device 700. The ring clamp 706, the screw 327 of FIG. 13 and other pressure fit elements are contemplated to immobilize the sleeve of this invention in the inserter.

Once assembled, an incision into the body is prepared and the sleeve 702 is positioned in or adjacent to the incision. The push-rod 710 is gently activated to advance the push-rod toward the distal portion of the device, thereby mobilizing the implant in the sleeve 702 and from the sleeve into the body. While either the blade embodiment or the push-rod embodiment will function with the flexible, deformable sleeves of this invention, the blades may be better suited for more fragile implants. Advantageously, the push-rod device in combination with the sleeve of this invention requires little force to mobilize an implant so that the likelihood of damaging the implant with the push-rod is low.

FIGS. 21–24 illustrate yet another embodiment of a sleeve supporting device or sleeve holder. Here, however, the sleeve holder is configured as an elastomeric, flexible hub or collar-like member 670. While most any material capable of stretching over a hand-piece as further described below will suffice, the holder 670 is preferably prepared from silicon, latex, urethane, thermoplastic rubber compounds (such as those sold under the trademark KRATON), or other suitable elastomeric materials (e.g., soft plastics). Ideally, sleeve holder 670 is sufficiently clear to permit visualization of an implant 672 within an implant delivery apparatus, such as a sleeve 674 when the sleeve is positioned in holder 670. Sleeve holder 670 includes a lumen 675 extending therethrough defining an interior surface that is slightly larger but generally and preferably in conformance with the surface of a tubular portion 676 of sleeve 674.

Figure 21:
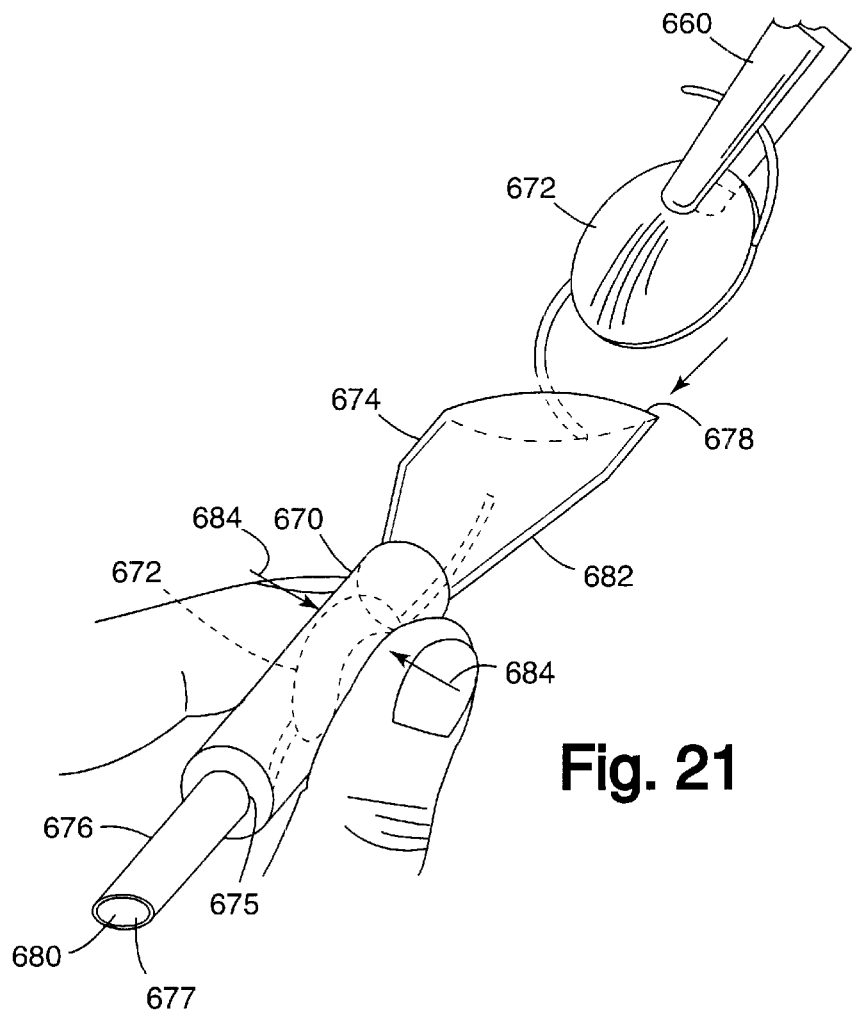
FIG. 21 is a perspective view of a sleeve holder in accordance with another embodiment of the invention.
Figure 22:
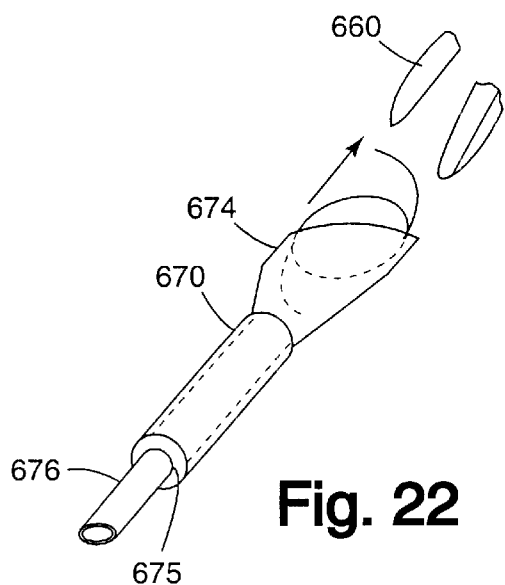
FIG. 22 is a perspective view of the sleeve holder of FIG. 21 illustrating removal of forceps from the sleeve.

In the embodiment illustrated in FIG. 21, the holder 670 has an exterior surface that defines a generally cylindrical shape. The lumen 675 defines a cylindrical interior surface for receiving the correspondingly shaped exterior of the tubular portion 676. While sleeve holder 670 is shown with an exterior shape substantially similar to its interior shape (i.e., cylindrical), the exterior surface of the sleeve holder can, in another embodiment, assume most any shape. For example, the exterior surface could be square in cross section while the lumen remains round. Likewise, lumen 675 can have a non-circular cross section (e.g., oval) to accommodate a sleeve having a similar shape. Thus, while the holder 670 is shown as a generally cylindrical tube (see FIGS. 21 and 22), those of skill in the art will recognize that a variety of holder shapes and sizes can be prepared to accommodate sleeves of most any shape.

While holder 670 can be made in most any proportion and configuration, it forms, at least in one embodiment, a cylinder having a lumen defining an inner diameter of about 1 mm to about 6 mm, a wall thickness of about 0.25 mm to about 2.5 mm, and a length ranging from at least 4 mm to about 25 mm. When used to deliver an intraocular lens, the holder 670 preferably has an inner diameter of about 2.0 mm to about 3.0 mm, a wall thickness of about 0.5 mm to about 1.5 mm, and a length of about 10 mm to about 15 mm.

Before insertion of lens 672, holder 670 is slid over sleeve 674 as shown in FIG. 21. Sleeve 674 includes a first opening 678 and a second opening 680 and preferably has dimensions similar to those described above with reference to sleeve 652 of FIG. 19. The sleeve, in one embodiment, transitions from first opening 678 to second opening 680 via a tapered portion 682. Between the tapered portion 682 and second opening 680 is tubular portion 676. A lumen 677 extends through the sleeve 674. The first opening is preferably flattened to accommodate implant insertion as already shown and described herein (see e.g., FIG. 2).

After lubricating the interior of the sleeve with a suitable friction-reducing agent or buffer, intraocular lens 672 is inserted into first opening 678 using forceps 660, fingers, or the like. The lens is urged into the first opening 678 and is positioned preferably past the tapered portion 682 of sleeve 674 and at least partially into tubular portion 676 of the sleeve as shown. The sleeve 674 is preferably able to distend or stretch to accommodate the additional bulk of forceps 660 when the forceps is introduced into the sleeve with the implant. Optionally, the implant can be deformed slightly to encourage folding in a desired direction when the implant is introduced into the sleeve, using, for example, lateral pressure while introducing the implant 672 into sleeve 674.

To prevent implant 672 from adhering to forceps 660 during removal of the latter, the holder 670 is gently compressed or squeezed, such as between a thumb and forefinger, as shown by arrows 684 in FIG. 21. By squeezing the holder 670, the tubular portion 676 is slightly dimpled or deformed, preferably adjacent to the lens 672 (shown in broken lines within tubular portion 676) and between the lens and the first opening 678. This localized deformation of the sleeve immobilizes the implant 672, preventing it from adhering to forceps 660 as the forceps is removed. By squeezing the sleeve as shown in FIG. 21, forceps 660 is easily removed from first opening 678 without unintentional removal of the implant 672 which, as demonstrated by FIG. 22, may occur if the implant is not immobilized.

Ideally, the shape and size of the holder 670 permits it to be easily and comfortably held in one hand while the other hand inserts the implant 672 into a sleeve within the holder. While not shown, the sleeve 674 may include other optional features such as pleats similar to pleats 38 shown in sleeve 20 of FIG. 2, for example.

The sleeve holder is preferably reusable and can optionally, along with the other components of this invention, be disposable or sterilizable such as by autoclaving or exposure to ethylene oxide or ultraviolet light.

Accordingly, the holder 670 provides an effective tool for gripping the sleeve during implant insertion and for immobilizing the lens during forceps removal. By merely altering the size and shape of the holder 670, it can accommodate most any sleeve size and configuration while still comfortably fitting within the hand of the typical user.

Figure 23:
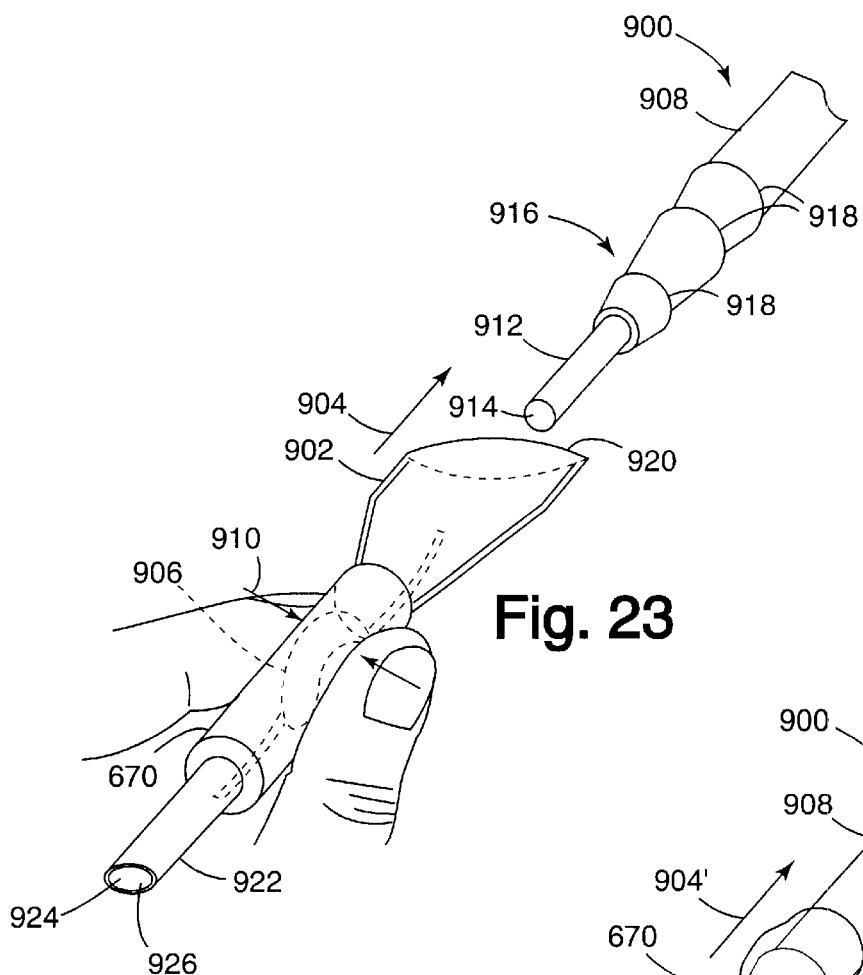
FIG. 23 is a perspective view of a sleeve with an intraocular lens for attachment to an insertor in accordance with another embodiment of the invention.

FIG. 23 illustrates an insertor for receiving a flexible, deformable sleeve in accordance with another embodiment of the present invention. An insertor 900 is shown along with a flexible sleeve 902 and a sleeve holder 670, the latter shown and described in FIGS. 21–22. A hand-piece 908 includes a pusher-element (not shown) or other means for mobilizing a push-rod 912. The push-rod 912 is preferably rounded at the tip 914 to minimize trauma to the implant when the implant is mobilized therein, but the push-rod tip 914 could also be flattened (as shown), grooved, or have most any other feature or shape. The push-rod 912 is preferably prepared from either the same or similar material as the hand piece or, alternatively, prepared from stainless steel, TEFLON, acrylic, vinyl, polysulfone, or the like.

The insertor 900 utilizes a first, barbed end 916 having a taper and forming one or more barbs 918. The push-rod 912 preferably extends from the hand-piece sufficiently that it can be positioned within a first opening 920 of the sleeve 902 as the two components are assembled. The first opening 920 may be swaged, flattened or rounded as already described herein in order to more easily receive the implant. The sleeve tapers from first opening 920 to a tubular portion 922 and terminates at a second opening 924. A lumen 926 extends through sleeve 902. The sleeve may include an implant such as an intraocular lens 906 as shown in FIG. 23. This implant may have been inserted into the sleeve using the methods described herein with reference to FIGS. 21 and 22.

To attach sleeve 902 to insertor 900, push-rod 912 is passed into first opening 920 and the sleeve and holder 670 are moved towards the insertor, as generally indicated by arrow 904 in FIG. 23. A slight squeezing force 910 can be applied to holder 670 to immobilize implant 906 and to better grip sleeve 902.

Figure 24:
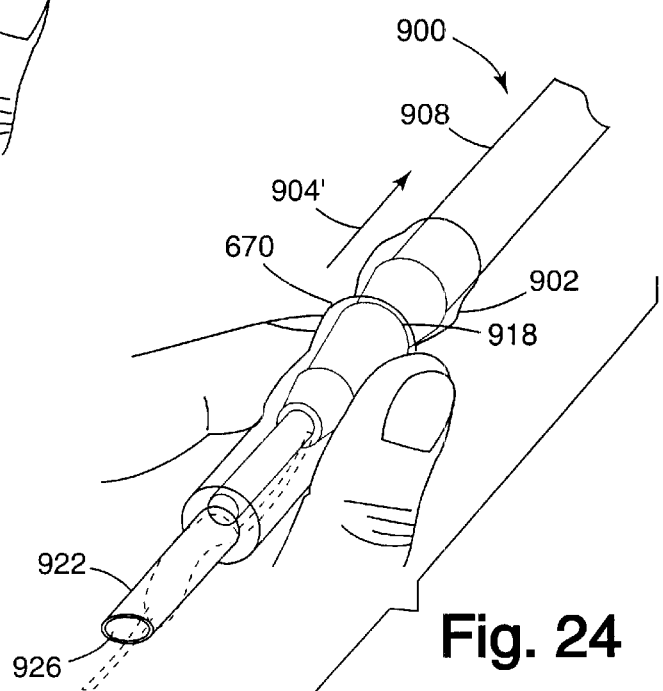
FIG. 24 is a perspective view of the sleeve and insertor of FIG. 23 as they are assembled.

As sleeve 902 approaches barbs 918, first opening distorts 920 (i.e., becomes round) to pass over the barbs. By grasping the holder and pushing in the direction indicated by arrow 904' in FIG. 24, the user can force the sleeve and insertor together. The continued application of force to holder 670 in the direction 904' causes the holder to slide over the sleeve and stretch and expand to traverse barbs 918 as also shown in FIG. 24. To ensure that the holder 670 slides easily over the sleeve 902, a lubricant may be provided therebetween.

Preferably, sleeve holder 670 is made from an elastomeric material as described herein that permits the holder to stretch from its original state to traverse the barbs 918 without tearing. Depending on the size of insertor 900 and the size and thickness of sleeve holder 670, holders that stretch from about 10% to about 250% from their unstretched diameter are contemplated.

When assembly is completed, sleeve holder 670 has expanded over barbs 918, trapping a portion of sleeve 902 between the holder and the barbs (see FIG. 24). The holder thus becomes a locking hub or collar much like the ring clamp 706 of FIG. 18a. When assembled, the push rod *912 is located in the tubular portion 922 proximal the implant 906. When the pusher element (not shown) is activated, the push rod 912 extends, forcing the implant 906 through the sleeve and injecting it into an incision (also not shown).*

A kit according to one embodiment of the present invention may include one or more of the hand-piece 908, sleeve 902, implant 906, a buffer or friction coating, and the holder 670. By combining embodiments of the sleeve and sleeve holder and optionally other elements as described in FIGS. 21–24 and elsewhere herein, an implant loading system or kit is provided.

FIGS. 25–29 illustrate yet other embodiments of insertor devices according to the present invention. FIG. 25 shows an insertor 1000 having a hand-piece 1001 with a distal end 1004 wherein a push rod 1002 extends therefrom. The distal end 1004 further includes a frustum or tapered portion 1006 and a retaining portion 1008. While tapered portion 1006 can have most any taper angle, tapered portion 1006, in one embodiment, includes a taper angle of about 0° to about 15°, and more preferably about 5° to about 7°. Distal end 1004 may alternatively be formed as a standard luer lock fitting which is commonly known in the medical arts.

A sleeve 1010 (similar or identical to sleeve 20 illustrated in FIG. 2 or sleeve 902 illustrated in FIG. 23) having an implant 1012 is then slid over the distal end 1004. The sleeve has a first end 1014 which, in one embodiment, defines a flattened portion (not shown but similar to sleeve 20 of FIG. 2) in its relaxed state but which expands to conform and surround the tapered portion 1006 of the insertor 1000 when assembled (see FIG. 25). In an alternate embodiment, a sleeve 1011 has a generally uniform cross-sectional shape, but has first end 1015 having longitudinal expansion slits or cuts 1016 as generally shown in FIG. 27. Cuts 1016 permit the sleeve to easily slide over the tapered portion 1006.

A clamping collet 1018 forming a sleeve holder as shown in FIG. 25 is also provided. The collet has an internal retaining portion 1019 and an internal-frustum or tapered portion 1021 (see FIG. 29). The retaining portion 1019 is adapted to couple to retaining portion 1008 while tapered portion 1021 is adapted to conform with tapered portion 1006 (i.e., portion 1021 has a taper angle substantially similar to the taper angle of portion 1006). The collet 1018 further defines a lumen 1009 as shown in FIG. 25.

In one embodiment, collet 1018 is made from a flexible material such as rubber and can be used to assist in loading implant 1012 into sleeve 1010 in a manner similar to that described with respect to sleeve holder 670 illustrated in FIG. 21. After loading the implant, the sleeve is slid over distal end 1004 and collet 1018 is slid over the sleeve in the direction 1020 until retaining portion 1019 engages retaining portion 1008, thereby securing the sleeve between the collet and the hand-piece.

The retaining portions 1019 and 1008 can be formed in a variety of ways without departing from the scope of the invention. For example, one or both of the surfaces may have protrusions such as a helical thread formed thereon. The helical threads may then be threadably engaged (e.g., rotated like a nut and bolt) or, where collet 1018 is flexible, the collet may slide longitudinally over the insertor where the threads then interlock. In addition to threads, one or more of the retaining portions may form barbs, snap-fittings or other similar features that engage one another.

In another embodiment, collet 1018 is made from a less flexible substance (e.g., hard plastic, stainless steel). Here, the retaining portions 1019 and 1008 may form mating helical threads. During assembly, implant 1012 is placed within the sleeve using one of the various methods described herein. Collet 1018 is then placed over sleeve 1010 and pushed towards the distal end of the insertor as generally represented by arrow 1020 (FIG. 25). The sleeve then extends through the lumen 1009. Retaining portion 1019 (FIG. 29) is then threadably secured to retaining portion 1008, thereby immobilizing sleeve 1010. The collet may include gripping protrusions 1022 to assist in turning the collet 1018 as shown in FIG. 25. Once collet is tightened to distal end 1004, the sleeve is restrained between tapered portion 1006 of distal end 1004 and tapered portion 1021 of collet 1018 as generally illustrated in FIG. 29.

FIGS. 26 and 28 illustrate variations of the embodiment of the insertor described in FIGS. 25 and 29. Here, an insertor 1050 is provided having a hand-piece 1051 terminating at a distal end, the distal end having a frustum or tapered portion 1054. In one embodiment, the taper angle 1056 (see FIG. 28) is slight, preferably from about ½° to about 3°. This is sufficient to hold and lock a sleeve 1058 to the insertor as described below. However, other embodiments using different taper angles are also contemplated.

FIG. 26 shows grooves 1060 on tapered portion 1054. The grooves 1060 assist in securing sleeve 1058 as further described below. While shown with longitudinal grooves, tapered portion 1054 may alternatively include circumferential grooves (see e.g., FIG. 28), serrations, barbs, or other surface irregularities that assist in securing the sleeve 1058.

Like the embodiment of FIG. 25, the sleeve 1058 has a first end 1062 that is slid over the distal end of the insertor 1050 as shown in FIG. 26. First end is 1062 of sleeve 1056 can be flattened or folded (see e.g. FIG. 2) or it may be a straight tube with expansion slits like tube 1011 shown in FIG. 27.

Once the first end 1062 is placed over the distal end as shown in FIG. 26, a sleeve holder forming a wedging collet 1064 having a lumen 1066 and having the same or similar taper angle as the tapered portion 1054 is slid over the sleeve 1058 and onto the distal end as shown in cross-section in FIG. 28. By adequately forcing the wedging collet 1064 over the tapered portion 1054 of the insertor 1050, friction between the tapered portion (assisted by grooves 1060), sleeve, and wedging collet keeps the sleeve immobilized.

In one embodiment, collet 1064 is made from a flexible material such as rubber. As such, it can be used to assist in pre-loading of an implant (not shown) into sleeve 1058 before the sleeve is attached to the distal end in a manner similar to that described with respect to sleeve holder 670 illustrated in FIG. 21.

Like the embodiments described with reference to FIGS. 18*a*–18*c*, the embodiment shown in FIGS. 23–29 require first that an incision into the body be prepared and the sleeve then be positioned in or adjacent to the incision. The push-rod is then gently activated to advance the implant toward the distal portion of the sleeve and into the body.

It is noted that, while described in terms of push rod configurations, the embodiments illustrated in FIGS. 23–29 may also be adapted to the blade-type pusher as described and illustrated elsewhere in this specification (see e.g., FIG. 1).

In another aspect of this invention, the invention relates to a method for making a sleeve of this invention. A variety of methods are available in the art for making the sleeves of this invention from a variety of flexible, distendable, compressible materials. These methods include, but are not limited to, injection molding and pressing or compressive forces to form the sleeve from existing materials.

In a preferred embodiment, a compressive force is used to compress and distend a flexible and distendable material to form a sleeve. In a preferred method, ETFE or PTFE tubing is subjected to a squeezing and compressive force such as a hydraulic or screw-jack press to form, squeeze and flatten the tubing into the widened first opening of the sleeve so that the width is wider than the initial tubing diameter and to form the tapered portion of the sleeve. Heat can be added to the compressive force to ease compression, for example, for higher tensile strength plastics. Preferred temperatures should be below the melting temperature of the tubing and preferably for PTFE tubing less than about 232° C. However, in a preferred embodiment the press does not include a heat source and the press uses cold flow squeezing to flatten and expand the PTFE or ETFE tubing to form a wider implant loading zone (i.e., the first opening of the sleeve) relative to the tubing diameter.

Figure 20:
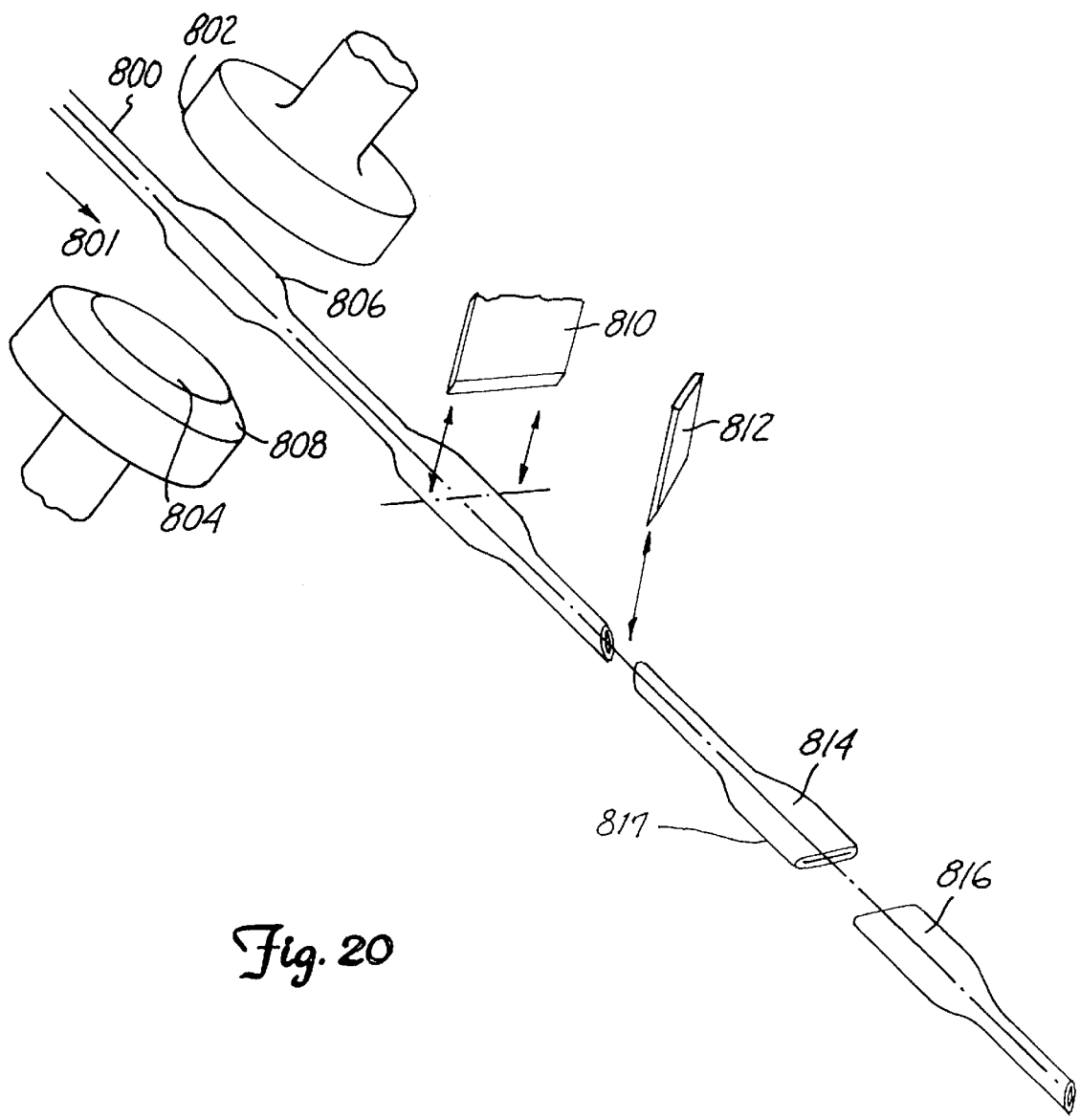
FIG. 20 illustrates a preferred method of this invention for preparing a sleeve.

Referring now to FIG. 20, and following the direction of arrow 801, FIG. 20 illustrates a preferred method for producing the sleeves of this invention using preformed tubing 800, where the tubing 800 is malleable and substantially transparent to permit visualization of an implant when positioned therein and where the tubing is suitable to distension and compression.

The tubing 800 is positioned between a press, preferably having two compressive surfaces 802 and 804. Tubing 800 is preferably extruded tubing and preferably PTFE or ETFE. Preferred PTFE tubing is about 2.5 mm in diameter with a preferred wall thickness of about 0.15 mm but those of ordinary skill in the art will recognize that a variety of sizes of tubing and a variety of compressive forces can be used to prepare sleeves of this invention in a variety of sizes and wall thicknesses without undue experimentation. The tubing is subjected to a compressive force sufficient to permanently flatten or otherwise crease and distend and compress the tubing. A preferred distended tubing shape is provided in FIG. 20 as distended tubing portion 806. The distended shape results in the formation of edges 817. Preferred distension and compressive forces will depend on the tubing material but are preferably between about 1,000 psi to about 25,000 psi and more preferably from about 5,000 psi to about 10,000 psi. Preferably the force is applied perpendicular to the tubing. Referring again to compressive surfaces 802 and 804, preferably at least one of the compressive surfaces includes a sloping portion 808 that slopes away from at least one of the compressive surfaces. The angle of the sloping portion relative to the compressive surface can vary but is preferably at least 0.5° and in a preferred embodiment is about 1°. Preferred post-compression wall thicknesses for 2.5 mm PTFE tubing are about 0.01 mm to about 0.10 mm with a preferred post-compression wall thickness of about 0.08 mm. Preferably the post-compression wall thickness of the sleeve is less than two-thirds and preferably about one-half of the original wall thickness of the non-compressed tubing and is preferably further distended at least 1.6 of the original diameter of the tubing and more preferably about 3 times the diameter and preferably from about 2 to about 4 times the original diameter of the tubing Following application of a compressive force, the distended tubing portion 806 is cut, such as with a cutting blade 810 or another device. In addition, the tubing is further cut in a non-distended region, if needed, as illustrated using cutting blade 812. Cutting blade 812 can be angled, if desired, to produce a beveled effect. Advantageously, using this method, each region of distended tubing can be used to prepare two sleeves 814 and 816 as illustrated in FIG. 20. The mechanics behind the compressive surfaces can vary such that a mechanized press, a hydraulic press, a hand cranked press or the like can be used, as suited to a particular application. Further, the sleeves can be prepared individually, or, as illustrated in FIG. 20 in a production line. As discussed above, the final length of the sleeve, the shape of the distended portion and the length of the non-distended portion as well as the grade of the taper of the sleeve can vary depending on the dimensions of the insertor.

It will be appreciated by those skilled in the art that while the invention has been described above in connection with particular embodiments and examples, the invention is not necessarily so limited and that numerous other embodiments, examples, uses, modifications and departures from the embodiments, examples and uses may be made without departing from the inventive scope of this application.

What is claimed is:

1. A system for introducing an implant into the body comprising:
   a flexible, compressible sleeve wherein the sleeve comprises a first opening and a second opening and a first lumen extending through the sleeve, wherein the sleeve is prepared from a non-opaque material and wherein the width of the first opening is larger than the width of the second opening;
   a sleeve holder prepared from a substantially flexible material and comprising a second lumen extending therethrough, wherein the second lumen is adapted to substantially conform to the shape of the sleeve;
   an implant positioned within the first lumen; and
   a hand-piece having a first end, the first end adapted to be received within the first opening of the sleeve, wherein the first end of the hand-piece comprises at least one circumferential barb.

2. The system of claim 1 wherein the sleeve holder is adapted to expand such that the second lumen slides over the at least one circumferential barb.

3. The system of claim 1 wherein the sleeve is immobilized between the sleeve holder and the at least one circumferential barb.

4. An apparatus for implanting an ocular implant into an eye, the apparatus comprising:
   a flexible, compressible sleeve wherein the sleeve comprises a first opening and a second opening and a first lumen extending through the sleeve;
   a hand-piece having a first end, the first end adapted to couple with the first opening of the sleeve;
   a sleeve holder prepared from a substantially malleable material and comprising a second lumen extending therethrough, wherein the sleeve holder is adapted to stretch over the sleeve and the first end of the hand-piece to secure the sleeve thereto; and
   a pusher element operatively coupled to the hand-piece.

5. The apparatus of claim 4 further comprising an ocular implant in the sleeve, wherein the pusher element is adapted to eject the implant from the sleeve and into an incision in the eye.

6. The apparatus of claim 4 further comprising a buffer or lubricating agent within the sleeve.

7. A system for loading an implant comprising:
   a flexible, compressible sleeve wherein the sleeve comprises a first opening and a second opening and a first lumen extending through the sleeve, wherein the sleeve is prepared from a non-opaque material and wherein the width of the first opening is larger than the width of the second opening; and
   a sleeve holder prepared from a substantially flexible material and comprising a second lumen extending therethrough, wherein the second lumen is adapted to substantially conform to the shape of the sleeve, and wherein the sleeve is positioned within the second lumen.

8. The system of claim 7, wherein an implant is positioned within the first lumen and immobilized by the application of a lateral compressive force applied to the sleeve holder proximal the implant.

9. A system for introducing an implant into the body comprising:
   a flexible, compressible sleeve wherein the sleeve comprises a first opening and a second opening and a first lumen extending through the sleeve, wherein the sleeve is prepared from a non-opaque material and wherein the width of the first opening is larger than the width of the second opening;
   a sleeve holder prepared from a substantially flexible material and comprising a second lumen extending therethrough, wherein the second lumen is adapted to substantially conform to the shape of the sleeve;

an implant positioned within the first lumen; and a hand-piece having a first end, the hand-piece capable of coupling to and retaining the sleeve, wherein the first opening of the sleeve is adapted to couple to the first end of the hand-piece.

10. A system for introducing an implant into the body comprising:
- a flexible, compressible sleeve wherein the sleeve comprises a first opening and a second opening and a first lumen extending through the sleeve, wherein the sleeve is prepared from a non-opaque material and wherein the width of the first opening is larger than the width of the second opening;
- a sleeve holder prepared from a substantially flexible maternal and comprising a second lumen extending therethrough, wherein the second lumen is adapted to substantially conform to the shape of the sleeve and is further adapted to surround a portion of the sleeve;
- an implant positioned within the first lumen; and
- a hand-piece having a first end, the hand-piece capable of coupling to and retaining the sleeve.

11. A system for introducing an implant into the body comprising:
- a flexible, compressible sleeve wherein the sleeve comprises a first opening and a second opening and a first lumen extending through the sleeve, wherein the sleeve is prepared from a non-opaque material and wherein the width of the first opening is larger than the width of the second opening;
- a sleeve holder prepared from a substantially flexible material and comprising a second lumen extending therethrough, wherein the second lumen is adapted to substantially conform to the shape of the sleeve;
- an implant positioned within the first lumen; and
- a hand-piece having a first end, the hand-piece capable of coupling to and retaining the sleeve, wherein the second lumen of the sleeve holder is adapted to couple to the first end of the hand-piece.

12. A system for introducing an implant into the body comprising:
- a flexible, compressible sleeve wherein the sleeve comprises a first opening and a second opening and a first lumen extending through the sleeve, wherein the sleeve is prepared from a non-opaque material and wherein the width of the first opening is larger than the width of the second opening;
- a sleeve holder prepared from a substantially flexible material and comprising a second lumen extending therethrough, wherein the second lumen is adapted to substantially conform to the shape of the sleeve;
- an implant positioned within the first lumen; and
- a hand-piece having a first end, the hand-piece capable of coupling to and retaining the sleeve, wherein the sleeve holder surrounds a portion of the sleeve and further surrounds a portion of the first end of the hand-piece, where the sleeve is restrained by the second lumen of the sleeve holder against the first end of the hand-piece.

13. A system for introducing an implant into the body comprising:
- a flexible, compressible sleeve wherein the sleeve comprises a first opening and a second opening and a first lumen extending through the sleeve, wherein the sleeve is prepared from a non-opaque material and wherein the width of the first opening is larger than the width of the second opening;
- a sleeve holder prepared from a substantially flexible material and comprising a second lumen extending therethrough, wherein the second lumen is adapted to substantially conform to the shape of the sleeve;
- an implant positioned within the first lumen; and
- a hand-piece having a first end, the hand-piece capable of coupling to and retaining the sleeve, wherein the first end of the hand-piece comprises at least one surface protrusion.

14. The system of claim 13, wherein the at least one surface protrusion comprises a circumferential barb.

15. The system of claim 13, wherein the at least one surface protrusion comprises a helical tread.

16. A system for introducing an implant into the body comprising:
- a flexible, compressible sleeve wherein the sleeve comprises a first opening and a second opening and a first lumen extending through the sleeve, wherein the sleeve is prepared from a non-opaque material and wherein the width of the first opening is larger than the width of the second opening;
- a sleeve holder prepared from a substantially flexible material and comprising a second lumen extending therethrough, wherein the second lumen is adapted to substantially conform to the shape of the sleeve;
- an implant positioned within the first lumen; and
- a hand-piece having a first end, the hand-piece capable of coupling to and retaining the sleeve, wherein the first end of the hand-piece comprises a tapered portion.

17. A system for introducing an implant into the body comprising:
- a flexible, compressible sleeve wherein the sleeve comprises a first opening and a second opening and a first lumen extending through the sleeve, wherein the sleeve is prepared from a non-opaque material and wherein the width of the first opening is larger than the width of the second opening;
- a sleeve holder prepared from a substantially flexible material and comprising a second lumen extending therethrough, wherein the second lumen is adapted to substantially conform to the shape of the sleeve;
- an implant positioned within he first lumen; and
- a hand-piece having a first end, the hand-piece capable of coupling to and retaining the sleeve, wherein the first end of the hand-piece comprises at least one surface protrusion and a tapered portion.

18. A system for introducing an implant into the body comprising:
- a flexible, compressible sleeve wherein the sleeve comprises a first opening and a second opening and a first lumen extending through the sleeve, wherein the sleeve is prepared from a non-opaque material and wherein the width of the first opening is larger than the width of the second opening;
- a sleeve holder prepared from a substantially flexible material and comprising a second lumen extending therethrough, wherein the second lumen is adapted to substantially conform to the shape of the sleeve;
- an implant positioned within the first lumen; and
- a hand-piece having a first end, the hand-piece capable of coupling to and retaining the sleeve, wherein the hand-piece further includes means for ejecting the implant from the sleeve.

19. The system of claim 18, wherein the means for ejecting the implant is a push-rod.

20. A system for introducing an implant into the body comprising:
- a flexible, compressible sleeve wherein the sleeve comprises a first opening and a second opening and a first lumen extending through the sleeve, wherein the sleeve is prepared from a non-opaque material and wherein the width of the first opening is larger than the width of the second opening, and wherein the sleeve comprises at least one longitudinal slit proximate the first opening;
- a sleeve holder prepared from a substantially flexible material and comprising a second lumen extending therethrough, wherein the second lumen is adapted to substantially conform to the shape of the sleeve;
- an implant positioned within the first lumen; and
- a hand-piece having a first end, the had-piece capable of coupling to and retaining the sleeve.

21. A system for introducing an implant into the body comprising: a flexible, compressible sleeve wherein the sleeve comprises a first opening and a second opening and a first lumen extending through the sleeve, wherein the sleeve is prepared from a non-opaque material and wherein a size of the first opening of the sleeve is greater than a size of the second opening of the sleeve;
- a sleeve holder prepared from a substantially flexible material and comprising a second lumen extending therethrough, wherein the second lumen is adapted to substantially conform to the shape of the sleeve;
- an implant positioned within the first lumen; and
- a hand-piece having a first end, the hand-piece capable of coupling to and retaining the sleeve.

22. A kit comprising:
- a flexible, compressible sleeve wherein the sleeve comprises a first opening and a second opening and a first lumen extending through the sleeve, wherein the sleeve is prepared from a non-opaque material and wherein the width of the first opening is larger than the width of the second opening;
- a sleeve holder prepared from a substantially elastomeric material and comprising a second lumen extending therethrough, wherein the second lumen is adapted to receive and substantially conform to the shape of the sleeve;
- an implant positioned within the first lumen; and
- a hand-piece having a first end, the first end adapted to couple with the first opening of the sleeve, wherein the first end of the hand-piece further comprises at least one circumferential barb.

23. The kit of claim 22, wherein the first end of the hand-piece is positioned within the first opening of the sleeve and the sleeve holder is positioned to surround the first end of the hand-piece and at least a portion of the sleeve, thereby immobilizing the sleeve between the second lumen and the at least one circumferential barb.

* * * * *